United States Patent
van den Engh et al.

(10) Patent No.: US 9,778,165 B2
(45) Date of Patent: Oct. 3, 2017

(54) LIGHT COLLECTION SYSTEMS AND METHODS FOR MAKING AND USING THEREOF

(71) Applicant: Becton, Dickinson and Company, Franklin Lakes, NJ (US)

(72) Inventors: Gerrit Jan van den Engh, Concrete, WA (US); Brian R. Wadey, Sumner, WA (US); Veronica Lauren Kersten, Bellevue, WA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/053,929

(22) Filed: Feb. 25, 2016

(65) Prior Publication Data
US 2016/0258859 A1 Sep. 8, 2016

Related U.S. Application Data

(60) Provisional application No. 62/129,570, filed on Mar. 6, 2015.

(51) Int. Cl.
*G01N 15/14* (2006.01)
*G01N 15/10* (2006.01)

(52) U.S. Cl.
CPC ..... *G01N 15/1434* (2013.01); *G01N 15/1459* (2013.01); *G01N 15/1463* (2013.01); *G01N 2015/1006* (2013.01)

(58) Field of Classification Search
CPC ................................................ G01N 15/1434
See application file for complete search history.

(56) References Cited

U.S. PATENT DOCUMENTS

| 4,600,302 | A | 7/1986 | Sage, Jr. |
| 5,475,487 | A | 12/1995 | Mariella, Jr. et al. |
| 6,707,555 | B1 * | 3/2004 | Kusuzawa ........... G01N 21/474 356/436 |

(Continued)

FOREIGN PATENT DOCUMENTS

JP       2008-116422 A       5/2008

OTHER PUBLICATIONS

Huh et al., "Microfuildic for flow cytometric analysis of cells and particles", Physiological Measurement, 2005, vol. 26, No. 3, pp. R73-R98.

(Continued)

*Primary Examiner* — David Porta
*Assistant Examiner* — Hugh H Maupin
(74) *Attorney, Agent, or Firm* — Khin K. Chin; Bret E. Field; Bozicevic, Field & Francis LLP

(57) ABSTRACT

Systems for collecting light (e.g., in a flow stream) are described. Light collection systems according to embodiments include: a mount having an orifice for receiving light, an adapter configured for attaching a camera to the mount and a fastener for attaching a lens to the distal end of the mount and a releasably attachable connecter that is configured for coupling to an orifice plate and an aligner that is configured to couple with an aligner on the mount and maintain optical alignment between the mount and connector. Methods for coupling a connector and a mount are also described. Systems and methods for measuring light emitted by a sample (e.g., in a flow stream) are also provided.

23 Claims, 7 Drawing Sheets

(56) References Cited

U.S. PATENT DOCUMENTS

| | | |
|---|---|---|
| 6,813,017 B1 | 11/2004 | Hoffman et al. |
| 2003/0190262 A1 | 10/2003 | Blazewicz et al. |
| 2009/0299196 A1 | 12/2009 | Bawendi et al. |
| 2010/0167413 A1* | 7/2010 | Lundquist ........ G01N 27/44721 436/172 |
| 2010/0220315 A1 | 9/2010 | Morrell et al. |
| 2010/0278480 A1 | 11/2010 | Vasylyev |
| 2010/0328664 A1 | 12/2010 | Luscher |
| 2012/0013728 A1 | 1/2012 | Matsuo |
| 2012/0078531 A1 | 3/2012 | Lo et al. |

OTHER PUBLICATIONS

Lee et al., "Micro flow cytometers with buried SU-8/SOG optical waveguides", Sensors and Actuators A: Physical, 2003, vol. 103, No. 1, pp. 165-170.

\* cited by examiner

LIGHT COLLECTION SYSTEMS AND METHODS FOR MAKING AND USING THEREOF

CROSS-REFERENCE TO RELATED APPLICATIONS

This application claims priority to U.S. Provisional Patent Application Ser. No. 62/129,570 filed Mar. 6, 2015, the disclosure of which application is incorporated herein by reference.

INTRODUCTION

Flow cytometry is a technique used to characterize and sort biological material, such as cells of a blood sample or particles of interest in any other type of biological or chemical sample. A flow cytometer typically includes a sample reservoir for receiving a fluid sample, such as a blood sample, and a sheath reservoir containing a sheath fluid. The flow cytometer transports the particles (including cells) in the fluid sample as a cell stream to a flow cell, while also directing the sheath fluid to the flow cell. Within the flow cell, a liquid sheath is formed around the cell stream to impart a substantially uniform velocity on the cell stream. The flow cell hydrodynamically focuses the cells within the stream to pass through an irradiation source at an interrogation point.

Flow cytometry may be used to record distributions or physically sort the biological material. In flow cytometry, one or more compounds in a flow stream are irradiated with light. As components of the flow stream are irradiated, light is emitted and scattered. Variations in the materials, such as morphologies or fluorescent label, may cause variations in the observed light and these variations allow for characterization and separation. To quantify these variations, the light is collected and directed to the surface of a detector. The amount of light that reaches the detector can impact the overall quality of the optical signal outputted by the detector. The amount of light that reaches the detector can be raised by increasing the surface area of the detector or by increasing collection of the light from the sample.

SUMMARY

Aspects of the present disclosure include optically aligned light collection systems. Systems according to certain embodiments include a mount having an orifice for receiving light, an adapter configured to attach a camera to the mount, an aligner at the distal end of the mount and a fastener for attaching a lens. Systems also include a connector that is configured to be coupled to an orifice plate and includes an aligner positioned at a proximal end of the connector for releasably coupling to and maintaining optical alignment between the mount, the orifice plate and an optical collection component. In some embodiments, the light collection system further includes an optical collection component that is in optical alignment with the mount and connector. For example, the optical collection component may be a free-space light relay system or a fiber optics light relay system. One or more orifice plates may be positioned between the connector and the optical collection component. In some embodiments, the aligners are protrusions, grooves, notches, countersinks, counter-bores or holes, such as cylindrical or polygonal shaped dowels. The subject systems also include fasteners, such as to attach a lens to a distal end of the mount as well as to couple an optical collection component to the distal end of the connecter. For example, the fastener may be a magnet, a latch, a hinge, a tether, a hook and loop fastener, a screw thread or some combination thereof.

Aspects of the disclosure also include methods for assembling and optically aligning components of a light collection system. Methods according to certain embodiments include coupling a connector to a mount by connecting a first aligner at the proximal end of the connector to a second aligner at the distal end of the mount, attaching an orifice plate to the distal end of the connector and coupling an optical collection system to the distal end of the connector. In embodiments, connecting the first aligner to the second aligner is sufficient to optically align the mount and orifice plate with the optical collection system. In some embodiments, the aligners are protrusions (e.g., polygonal-shaped protrusions) and recesses (e.g., polygonal-shaped notches, countersinks or counter-bores) and methods include inserting the protrusions into the recesses. In certain embodiments, the distal end of the connector is coupled to a free-space light relay system. In other embodiments, the distal end of the connector is coupled to a fiber optics light relay system.

Aspects of the present disclosure also include systems for measuring light from a sample in a flow stream. In certain embodiments, systems include a light source, a detector that measures one or more wavelengths of light and an optically aligned light collection system that includes: a mount having an orifice for receiving light, an adapter that couples to a camera, an aligner at the distal end of the mount and a fastener for attaching a lens, a connector that is configured to be coupled to an orifice plate and includes an aligner at the proximal end of the connector that releasably couples and maintains optical alignment between the mount, the orifice plate and an optical collection component. In some embodiments, the light collection system further includes an optical collection component that is in optical alignment with the mount and connector. For example, the optical collection component may be a free-space light relay system or a fiber optics light relay system. In some embodiments, the system is a flow cytometer. The system may also include one or more of a focusing lens, a magnifying lens, a de-magnifying lens, collimating lens and a wavelength separator (e.g., a cutoff filter).

Aspects of the disclosure also include methods for irradiating a sample in a flow stream in an interrogation field with a light source, collecting and detecting light from the sample in the flow stream with the subject optically aligned light collection systems and measuring the detected light at one or more wavelengths. In some embodiments, light is collected and relayed to a detector by a free-space light relay system. In other embodiments, light is collected and relayed to a detector by a fiber optics light relay bundle. In certain embodiments, the light is collimated or spatially separated with one or more optical adjustment protocols.

Kits including one or more components of the subject optically aligned light collection systems are also provided. Kits according to certain embodiments, include one or more of the subject mounts and connectors, as well as orifice plates and an optical collection component. In some embodiments, kits may also include a two or more connectors that configured for releasably coupling to different types of optical collection components. For example, the subject kits may include a first connector that is configured to releasably couple to a fiber optics light relay system and a second connector that is configured to releasably couple to a free-space light relay system.

BRIEF DESCRIPTION OF THE FIGURES

The invention may be best understood from the following detailed description when read in conjunction with the accompanying drawings. Included in the drawings are the following figures.

DETAILED DESCRIPTION

Figure 1:
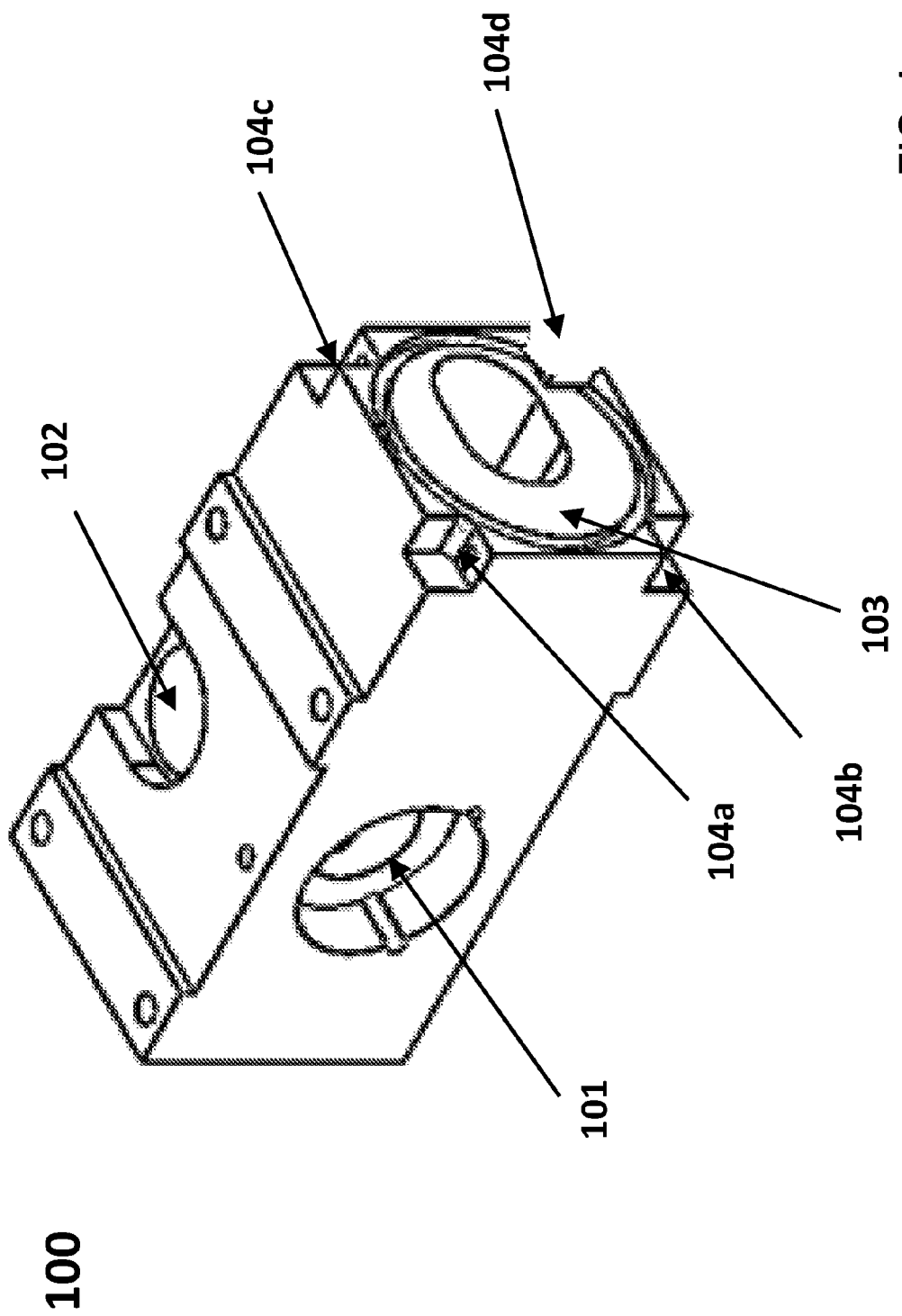
FIG. 1 depicts a perspective view of a mount according to certain embodiments of the present disclosure.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the present disclosure provides systems for optically aligning releasably attachable components. In further describing embodiments of the disclosure, light collection systems in accordance with embodiments of the invention are described first in greater detail. Next, methods for aligning components of the subject light collection systems are described. Systems and methods for measuring light emitted by a sample (such as in a flow stream of a flow cytometer) are also provided.

Optically Aligned Light Collection Systems

As summarized above, aspects of the present disclosure include optically aligned light collection systems configured for collecting light emitted by a sample (e.g., in a flow stream of a flow cytometer). As described in greater detail below, optically aligned light collection systems include a mount and a connector. In embodiments, the connector is in optical alignment with the mount and an optical collection component when the aligner of the connector is coupled to the aligner of the mount. The phrase "optically aligned" is used its conventional sense to refer to two or more optical components being positioned in line with each other such that the components have the same optical axis (i.e., are optically concentric). For example, optically aligned light collection systems according to embodiments of the present disclosure include a mount and a connector where the optical center of the mount is displaced from the optical center of the connector by 100 μm or less when measured orthogonally to the optical axis, such as 50 μm or less, such as 25 μm or less, such as 15 μm or less, such as 10 μm or less, such as 5 μm or less, such 2 μm or less, such as 1 μm or less, such as 0.5 μm or less, such as 0.1 μm or less, such as 0.05 μm or less, such as 0.01 μm or less, such as 0.005 μm or less and including where the optical center of the mount is displaced from the optical center of the connector by 0.001 μm or less when measured orthogonally to the optical axis. As described in greater detail below, after coupling an aligner at the distal end of the mount to an aligner at the proximal end of the connector, the optical center of a mount is displaced from the optical center of a connector by 500 μm or less when measured orthogonally to the optical axis, such as 400 μm or less, such as 250 μm or less, such as 100 μm or less, such as 50 μm or less, such as 25 μm or less, such as 15 μm or less, such as 10 μm or less, such as 5 μm or less, such 2 μm or less, such as 1 μm or less, such as 0.5 μm or less, such as 0.1 μm or less, such as 0.05 μm or less, such as 0.01 µm or less, such as 0.005 µm or less and including by 0.001 µm or less when measured orthogonally to the optical axis.

In some embodiments, the mount is releasably attached to the connector. The term "releasably" is used herein in its conventional sense to mean that the connector may be freely detached and re-attached to the mount. As described in greater detail below, in certain instances, the subject systems are configured such that a first connector that is coupled to the mount is detached and a second connector is coupled to the mount. In some embodiments, one or more of the connector and the mount may include a fastener for releasably coupling the connector to the mount. Suitable fasteners may include, but are not limited to, hook and loop fasteners, magnets, latches, notches, countersinks, counter-bores, grooves, pins, tethers, hinges, Velcro, non-permanent adhesives or a combination thereof.

In embodiments, the mount includes an orifice for receiving light (e.g., from a flow stream in a flow cytometer), an adapter configured to attach a camera to the mount, a fastener for attaching a lens and an aligner positioned at the distal end of the mount for coupling to and maintaining optical alignment with the connector. The mount has a proximal end and a distal end with walls between the distal end and proximal end that together form an inner chamber within the mount that is configured to convey light to the connector and optical collection component.

In some embodiments, the outer walls of the mount and the walls of the inner chamber have the same cross-sectional shape where cross-sectional shapes of interest include, but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. For example, both the outer walls of the mount and the walls of the inner chamber may have circular or oval cross sections or both the outer walls of the mount and the walls of the inner chamber may have polygonal (e.g., square) cross sections. In other embodiments, the outer walls of the mount and the walls of the inner chamber have different cross-sectional shapes. For example, the outer walls of the mount may have a polygonal (e.g., square) cross-section and the walls of the inner chamber may have a circular cross-section.

The length of the mount (as measured from the proximal end to the distal end of the outer walls of the mount) may vary ranging from 5 cm to 50 cm, such as from 6 cm to 45 cm, such as from 7 cm to 40 cm, such as from 8 cm to 35 cm and including from 10 cm to 30 cm, for example 11 cm. The size of the inner chamber within the mount may vary, where in some instances the length of the inner chamber may range from 1 cm to 50 cm, such as from 2.5 cm to 45 cm, such as from 5 cm to 40 cm, such as from 7.5 cm to 35 cm and including from 10 cm to 25 cm and the width of the inner chamber may range from 1 cm to 50 cm, such as from 2.5 cm to 45 cm, such as from 5 cm to 40 cm, such as from 7.5 cm to 35 cm and including from 10 cm to 25 cm. Where the inner chamber of the mount is cylindrical, the diameter may vary, in some embodiments, ranging from 1 cm to 10 cm, such as from 2 cm to 9 cm, such as from 3 cm to 8 cm and including from 4 cm to 7 cm. Accordingly, the volume of the inner chamber within the mount may vary, ranging from 0.01 to 100 cm$^3$, such as 0.05 to 50 cm$^3$, such as 0.1 to 25 cm$^3$, such as 0.5 to 15 cm$^3$, such as 0.75 to 10 cm$^3$, such as 1 to 7.5 cm$^3$, and including 2 to 5 cm$^3$.

In embodiments, the distal end of the mount is configured to be coupled to the proximal end of the connector such that coupling the proximal end of the connector and the distal end of the mount brings the connector and the mount into optical alignment. The mount distal end may include any number of aligners, so long as coupling of the aligners on the mount to the aligners on the connector is sufficient to position and maintain optical alignment between the mount and the connector. For example, the mount may include 2 or more aligners, such as 3 or more aligners, such as 4 or more aligners, such as 5 or more aligners, such as 7 or more aligners and including 10 or more aligners. Any suitable type of aligner may be employed, such as an alignment protrusion, an alignment rail, an alignment notch, an alignment groove, an alignment slot, an alignment countersink, an alignment counter-bore, an alignment hole or a combination thereof. For example, in some instances the mount distal end includes one or more protrusions, such as one or more press-fit dowels. In other instances, the mount distal end includes one or more recesses. In certain instances, the mount distal end includes one or more protrusions and one or more recesses.

The shape of aligners positioned at the distal end of the mount may vary, where cross-sectional shapes of interest include, but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In some embodiments, the aligners are cylindrically shaped. In other embodiments, the aligners are spherical. In yet other embodiments, the aligners are polygonal-shaped, such as square-shaped or rectangular.

The width of each aligner may vary, ranging in some instances from 1 mm to 25 mm, such as from 2 mm to 22 mm, such as from 3 mm to 20 mm, such as from 4 mm to 17 mm and including from 5 mm to 15 mm. The length of each aligner positioned at the distal end of the mount ranges from 1 mm to 50 mm, such as from 2 mm to 45 mm, such as from 3 mm to 40 mm, such as from 4 m to 35 mm, such as from 5 mm to 30 mm and including from 10 mm to 20 mm. Where the aligner positioned at the distal end of the mount is an alignment recess, such as a notch, a countersink, a counter-bore, a slot, a groove or a hole, the depth of the aligner may range from 1 mm to 50 mm, such as from 2 mm to 45 mm, such as from 3 mm to 40 mm, such as from 4 m to 35 mm, such as from 5 mm to 30 mm and including from 10 mm to 20 mm.

The aligners may be positioned at any location on the distal end of the mount. For example, in some embodiments one or more aligners are positioned adjacent to outer peripheral edge of the mount, such as 1 mm or more from the edge of the mount, such as 2 mm or more, such as 3 mm or more, such as 4 mm or more and including 5 mm or more from the outer edge of the mount. Where the cross-sectional shape of the mount is polygonal, one or more aligners may be positioned at the corners of the distal end of the mount. For example, where the mount has a square or rectangular cross-section, the aligners may be positioned at one or more of the four corners of the square or rectangle distal end of the mount.

Where the mount includes more than one aligner, the distance between each aligner may vary, being spaced apart by 2 mm or more, such as by 3 mm or more, such as by 5 mm or more, such as by 7 mm or more, such as by 10 mm or more and including by 25 mm or more. Where the mount includes three or more aligners, the distance between each aligner may be the same or different or a combination thereof. In some embodiments, the distance between each aligner is different. In other embodiments, each aligner is spaced equidistant from each other. In certain embodiments, the mount includes 4 aligners that are positioned equidistantly spaced along the outer edge of the mount distal end. For instance, the mount may include 4 polygonal-shaped (e.g., square or rectangular) recesses (e.g., complimentary to 4-polygonal-shaped protrusion in the connector) positioned at the four corners of the mount distal end.

The distal end of the mount also includes one or more fasteners configured for attaching a lens. In some cases, the lens is configured to be releasably attached to the distal end of the mount. In these embodiments, the lenses may be freely detached and re-attached to the mount. Suitable fasteners for releasably attaching the lens to the mount may include, but are not limited to, hook and loop fasteners, latches, notches, countersinks, counter-bores, grooves, pins, tethers, hinges, Velcro, non-permanent adhesives or a combination thereof. In certain instances, the distal end of the mount includes one or more screw threads for attaching a lens. In these embodiments, the lens may be screw threaded into the mount.

In some embodiments, one or more lenses are attached at the distal end of the mount, such as a lens that is screw threaded into the distal end of the mount. In these embodiments, the lenses are positioned to be optically concentric with the connector and optical collection component (as described in greater detail below) when the aligner at the distal end of the mount is coupled with the aligner at the proximal end of the connector. For example, when the aligner at the proximal end of the connector is coupled with the aligner at the distal end of the mount, the optical center of the lens attached at the distal end of the mount is displaced from the optical center of the connector by 100 µm or less when measured orthogonally to the optical axis, such as 50 µm or less, such as 25 µm or less, such as 15 µm or less, such as 10 µm or less, such as 5 µm or less, such 2 µm or less, such as 1 µm or less, such as 0.5 µm or less, such as 0.1 µm or less, such as 0.05 µm or less, such as 0.01 µm or less, such as 0.005 µm or less and including where the lens attached at the distal end of the mount is displaced from the optical center of the connector by 0.001 µm or less when measured orthogonally to the optical axis.

In embodiments, the mount lens may be any suitable lens for conveying light received by the mount to the optical collection component (described below) and may include, but is not limited to, a collimating lens, a focusing lens, a magnifying lens, a de-magnifying lens, or some other lens. Depending on the size of the mount, the width of the lens may vary, ranging from 1 cm to 20 cm, such as from 2 cm to 19 cm, such as from 3 cm to 18 cm, such as from 4 cm to 17 cm and including from 5 cm to 15 cm. The numerical aperture of the lens may also vary, ranging from 0.01 to 2.0, such as from 0.05 to 1.9, such as from 0.1 to 1.8, such as from 0.2 to 1.7, such as from 0.3 to 1.6, and including a numerical aperture ranging from 0.5 to 1.5. Likewise, the focal length of the lens varies, ranging from 0.1 mm to 20 mm, such as from 0.5 mm to 19 mm, such as from 1 mm to 18 mm and including from 2 mm to 15 mm. In some embodiments, the distal end of the mount includes a focusing lens having a magnification ratio from 0.1 to 0.95, such as a magnification ratio of from 0.2 to 0.9, such as a magnification ratio of from 0.3 to 0.85, such as a magnification ratio of from 0.35 to 0.8, such as a magnification ratio of from 0.5 to 0.75 and including a magnification ratio of from 0.55 to 0.7, for example a magnification ratio of 0.6. In other embodiments, the distal end of the mount includes one or more collimating lenses. For example, the mount in certain instances includes a single collimating lens. In other instances, the mount includes two collimating lenses.

In embodiments, the mount includes one or more orifices for receiving light into the internal cavity of the mount, such as receiving light from a flow stream in a flow cytometer. The orifice may be any suitable shape where cross-sectional shapes of interest include, but are not limited to: rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion. In certain embodiments, the orifice on the mount configured to receive light is a circular orifice. The size of the orifice may vary depending on shape, in certain instances, having an opening ranging from 0.5 mm to 50 mm, such as from 0.75 mm to 40 mm, such as from 1 mm to 30 mm and including from 5 mm to 25 mm. The mount may include any number of orifices for receiving light, such as 1 or more orifices, such as 2 or more orifices, such as 3 or more orifices, such as 5 or more orifices and including 10 or more orifices. In certain embodiments, the mount includes one orifice for receiving light.

In some embodiments, one or more of the orifices are positioned at the proximal end of the mount. In other embodiments, the orifices are positioned adjacent to the proximal end of the mount, such as along a side wall of the mount where the optical axis of the orifice (i.e., the axis of light collection by the orifice) is orthogonal to the longitudinal axis of the mount. In these embodiments, the orifice may be on a side wall of the mount at a position that is 1 mm or more from the proximal end of the mount, such as 2 mm or more, such as 3 mm or more, such as 5 mm or more, such as 10 mm or more, such as 15 mm or more, such as 25 mm or more, such as 50 mm or more and including 100 mm or more from the proximal end of the mount. Where the orifice is positioned in a side wall of the mount, the mount may further include one or more mirrors configured to redirect light collected by the orifice along the longitudinal axis of the mount.

In some embodiments, the mount also includes an adapter configured for coupling to a camera. The adapter may be any suitable attachment protocol configured for positioning to one or more cameras to the outer wall of the mount, such as 2 or more cameras, such as 3 or more cameras and including 4 or more cameras.

In certain instances, the adapter includes one or more fasteners for releasably or non-releasably attaching a camera to the mount. For example, the camera adapter may include a hook and loop fastener, one or more magnets, a latch, a notch, a countersink, a counter-bore, a series of grooves, slots, pins, tethers, hinges, a thread screw, one or more patches of Velcro, adhesive (permanent or non-permanent) or a combination thereof. In these embodiments, the mount is configured with an adapter that can be coupled to a camera, as desired, such as imaging sensors capable of capturing and converting an optical image into an electronic data signal, including but not limited to charge-coupled devices, semiconductor charge-coupled devices (CCD), active pixel sensors (APS), complementary metal-oxide semiconductor (CMOS) image sensors or N-type metal-oxide semiconductor (NMOS) image sensors. In some embodiments, the imaging sensor is a CCD camera. For example, the camera may be an electron multiplying CCD (EMCCD) camera or an intensified CCD (ICCD) camera. In other embodiments, the imaging sensor is a CMOS-type camera.

In certain embodiments, the adapter configured to couple to a camera may be located at any position on the mount. In some embodiments, the mount is located on a side wall of the mount. In other embodiments, the adapter is located on a top wall of the mount. In still other embodiments, the adapter is located on a bottom wall of the mount. The adapter may be positioned anywhere between the proximal and distal ends of the mount, as desired. For example, the adapter may be positioned at the proximal end of the mount. In other embodiments, the adapter configured to couple to a camera is positioned at the distal end of the mount. In still other embodiments, the adapter is positioned at a predetermined position from the proximal end of the mount, such as 1 mm or more from the proximal end, such as 2 mm or more, such as 5 mm or more, such as 10 mm or more, such as 15 mm or more, such as 25 mm or more, such as 35 mm or more and including 50 mm or more from the proximal end of the proximal end of the mount.

Where the subject light collection systems include more than one camera, each camera may be oriented with respect to the other (as referenced in an X-Z plane) at an angle ranging from 10° to 180°, such as from 15° to 170°, such as from 20° to 160°, such as from 25° to 150°, such as from 30° to 120° and including from 45° to 90°. In certain embodiments, each camera is oriented orthogonally (as referenced in an X-Z plane) to each other. For example, where the subject systems include two cameras, the first camera is oriented orthogonally (as referenced in an X-Z plane) to the second camera. In other embodiments, a first camera is positioned on the top of the mount and a second camera is positioned on the bottom of the mount.

Where the mount is coupled with more than one camera, the cameras may be the same or a combination of different types. For example, where the subject systems include two cameras, in some embodiments the first camera is a CCD-type device and the second camera is a CMOS-type device. In other embodiments, both the first and second cameras are CCD-type devices. In yet other embodiments, both the first and second cameras are CMOS-type devices.

FIG. 1 depicts a perspective view of a mount according to certain embodiments of the present disclosure. Mount 100 includes orifice 101 for collecting light from an irradiated sample (e.g., in a flow stream) and adapter 102 for coupling to an auxiliary device such as a rotatable mirror or a camera. Mount 100 also includes a fastener 103 for attaching a lens at the distal end of the mount as well as four aligners 104a, 104b, 104c and 104d for coupling with aligners at the proximal end of the connector (described below).

As summarized above, the subject light collection systems include a mount and a connector. In embodiments, the connector has a proximal end and distal end with walls between the distal end and proximal end that together form an inner chamber within the connector that is configured to convey light from the mount to the optical collection component. The outer walls of the connector and inner chamber within may have the same cross-sectional shape where cross-sectional shapes of interest include, but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. For example, both the outer walls of the connector and the walls of the inner chamber within may have circular or oval cross sections or both the outer walls of the connector and the inner walls of the chamber within may have polygonal (e.g., square) cross sections. In other embodiments, the outer walls of the connector and the walls of the inner chamber within have different cross-sectional shapes. For example, the outer walls of the connector may have a polygonal (e.g., square) cross-section and the walls of the inner chamber within may have a circular cross section.

The inner chamber within the connector may have the same or different cross-sectional shape as the inner chamber of the mount. In some instances, the cross-sectional shape of connector inner chamber is the same as that of the mount, such as where the inner chamber of both the mount and the connecter have a polygonal (e.g., square), circular or oval cross-section. In other instances, the cross-sectional shape of the connector inner chamber is different from the cross-sectional shape of the mount. For example, the connector inner chamber may have a polygonal (e.g., square) cross-section and the mount inner chamber may have a circular or oval cross-section.

The length of the connector (as measured from the proximal end to the distal end of the outer walls of the connector) may vary ranging from 1 cm to 50 cm, such as from 2 cm to 45 cm, such as from 3 cm to 40 cm, such as from 4 cm to 35 cm and including from 5 cm to 30 cm, for example 6 cm. The size of the inner chamber within the connector may vary, where in some instances the length of the inner chamber may range from 1 cm to 50 cm, such as from 2.5 cm to 45 cm, such as from 5 cm to 40 cm, such as from 7.5 cm to 35 cm and including from 10 cm to 25 cm and the width of the inner chamber may range from 1 cm to 50 cm, such as from 2.5 cm to 45 cm, such as from 5 cm to 40 cm, such as from 7.5 cm to 35 cm and including from 10 cm to 25 cm. Where the inner chamber of the connector has a circular cross-section, the diameter may vary, in some embodiments, ranging from 1 cm to 10 cm, such as from 2 cm to 9 cm, such as from 3 cm to 8 cm and including from 4 cm to 7 cm. Accordingly, the volume of the inner chamber within the connector may vary, ranging from 0.01 to 100 $cm^3$, such as 0.05 to 50 $cm^3$, such as 0.1 to 25 $cm^3$, such as 0.5 to 15 $cm^3$, such as 0.75 to 10 $cm^3$, such as 1 to 7.5 $cm^3$, and including 2 to 5 $cm^3$.

Where both the mount and connector have cylindrical inner chambers, the diameters of the mount and connector inner chambers may be the same or different. In certain embodiments, the diameter of the mount inner chamber and the connector inner chamber is the same. In other embodiments, the diameters differ, such as by 1% or more, such as by 2% or more, such as by 5% or more, such as by 10% or more, such as by 25% or more and including by 50% or more. For example, the diameters may differ by 0.1 mm or more, such as by 0.5 mm or more, such as by 1 mm or more, such as by 2 mm or more, such as by 3 mm or more and including by 5 mm or more. In some instances, the diameter of the mount inner chamber is greater than the diameter of the connector inner chamber. In other instances, the diameter of the connector inner chamber is greater than the diameter of the mount inner chamber.

In embodiments, the proximal end of the connector is configured to be coupled to the distal end of the mount. The proximal end of the connector includes one or more aligners that are configured to couple with aligners at the distal end of the mount. The connector may include any number of aligner so long as coupling of the aligners on the connector to the aligners on the mount is sufficient to position and maintain optical alignment between the mount and the connector. For example, the connector may include 2 or more aligners, such as 3 or more aligners, such as 4 or more aligners, such as 5 or more aligners, such as 7 or more aligners and including 10 or more aligners. Any suitable type of aligner may be employed, such as an alignment protrusion, an alignment rail, an alignment notch, an alignment countersink, an alignment counter-bore, an alignment groove, an alignment slot, an alignment hole or a combination thereof. For example, in some instances the connector proximal end includes one or more protrusions. In other instances, the connector proximal end includes one or more notches. In certain instances, the connector proximal end includes one or more protrusions and one or more notches.

The shape of aligners positioned at the proximal end of the connector may vary, where cross-sectional shapes of interest include, but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In some embodiments, the aligners are cylindrically shaped. In other embodiments, the aligners are spherical. In yet other embodiments, the aligners are polygonal-shaped, such as square-shaped or rectangular.

The width of each aligner on the connector proximal end may vary ranging from 1 mm to 25 mm, such as from 2 mm to 22 mm, such as from 3 mm to 20 mm, such as from 4 mm to 17 mm and including from 5 mm to 15 mm. The length of each aligner positioned at the proximal end of the connector ranges from 1 mm to 50 mm, such as from 2 mm to 45 mm, such as from 3 mm to 40 mm, such as from 4 m to 35 mm, such as from 5 mm to 30 mm and including from 10 mm to 20 mm. Where the aligner is an alignment recess, such as a notch, a countersink, a counter-bore, a slot, a groove or a hole, the depth of the aligner may range from 1 mm to 50 mm, such as from 2 mm to 45 mm, such as from 3 mm to 40 mm, such as from 4 m to 35 mm, such as from 5 mm to 30 mm and including from 10 mm to 20 mm.

The aligners may be positioned at any location on the proximal end of the connector. For example, in some embodiments one or more aligners are positioned adjacent to outer peripheral edge of the connector, such as 1 mm or more from the edge of the connector, such as 2 mm or more, such as 3 mm or more, such as 4 mm or more and including 5 mm or more from the outer edge of the connector. Where the cross-sectional shape of the connector is polygonal, one or more aligners may be positioned at the corners of the proximal end of the connector. For example, where the mount has a square or rectangular cross-section, the aligners may be positioned at one or more of the 4 corners of the square or rectangle distal end of the mount.

Where the connector includes more than one aligner, the distance between each aligner may vary, being spaced apart by 2 mm or more, such as by 3 mm or more, such as by 5 mm or more, such as by 7 mm or more, such as by 10 mm or more and including by 25 mm or more. Where the connector includes three or more aligners, the distance between each aligner may be the same or different or a combination thereof. In some embodiments, the distance between each aligner is different. In other embodiments, each aligner is spaced equidistant from each other. In certain embodiments, the connector includes 4 aligners that are positioned equidistantly spaced along the outer edge of the mount distal end. For instance, the connector may include 4 polygonal-shaped (e.g., square or rectangular) recesses (e.g., complimentary to 4-polygonal-shaped protrusion in the mount) positioned at the four corners of the connector distal end.

In some embodiments, the surfaces of aligners are substantially flat, such as to maximize contact between with aligners of the connector and the mount. By "substantially flat" is meant that the walls of the aligner exhibit little to no deviation along its surface, such as where crevices or protrusions along the aligner walls are 100 µm or less as measured from the wall surface, such as 50 µm or less, such as 25 µm or less, such as 15 µm or less, such as 10 µm or less, such as 5 µm or less, such 2 µm or less, such as 1 µm or less, such as 0.5 µm or less, such as 0.1 µm or less, such as 0.05 µm or less, such as 0.01 µm or less, such as 0.005 µm or less and including by 0.001 µm or less as measured from the wall surface. For example, where the mount distal end includes one or more protrusions, the outer walls (i.e., top and side surfaces) of the protrusions are substantially flat to maximize contact with the inner walls of recesses (i.e., bottom and side walls) positioned in the connector proximal end. Where the mount distal end includes one or more recesses, the inner walls (i.e., bottom and side walls) of the recesses are substantially flat to maximize contact with the outer walls (i.e., top and side surfaces) of the protrusions positioned at the connector proximal end.

Where the length of the alignment protrusion is the same as the depth of the alignment recess, when coupled together the distal end of the mount may be in physical contact with proximal end of the connector. Where the length of the alignment protrusion is greater than the depth of the alignment recess, when coupled together the distal end of the mount may be spaced apart from the proximal end of the connector by 1 mm or more, such as 2 mm or more, such as 3 mm or more, such as 5 mm or more and including by 10 mm or more.

Figure 2:
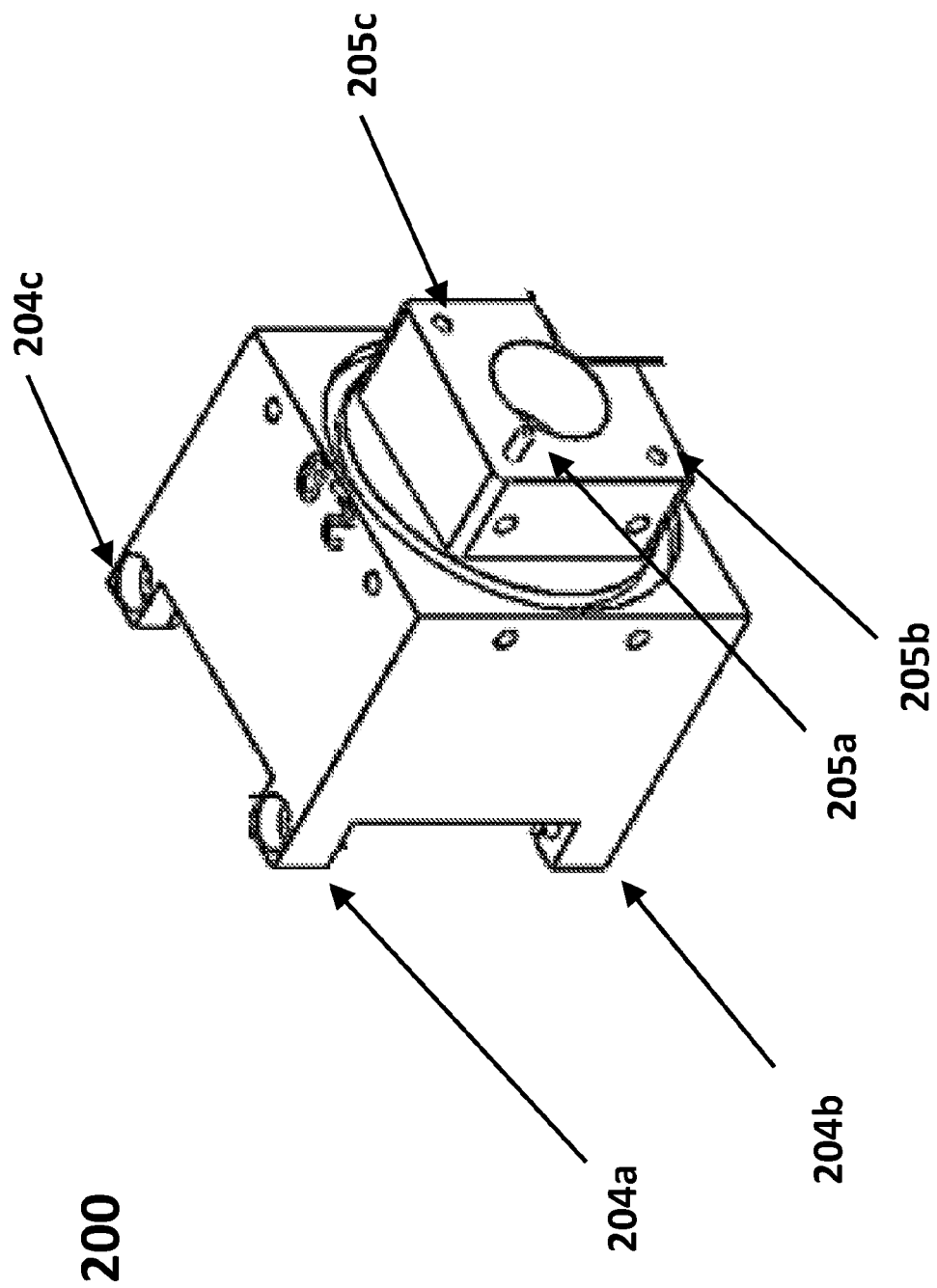
FIG. 2 depicts a perspective view of a connector according to certain embodiments of the present disclosure.

FIG. 2 depicts a perspective view of a connector according to certain embodiments of the present disclosure. Connector 200 includes a proximal end and a distal end, where the proximal end includes aligners 204a, 204b and 204c which couple to aligners at the distal end of the mount (depicted in FIG. 1 above). Connector 200 also includes a distal end that is configured to be coupled to an orifice plate and an optical collection component with screws that are inserted through the corners of the orifice plate and connector. Connector 200 includes screw holes (205a, 205b and 205c) for coupling to the orifice plate and optical collection component.

Figure 3:
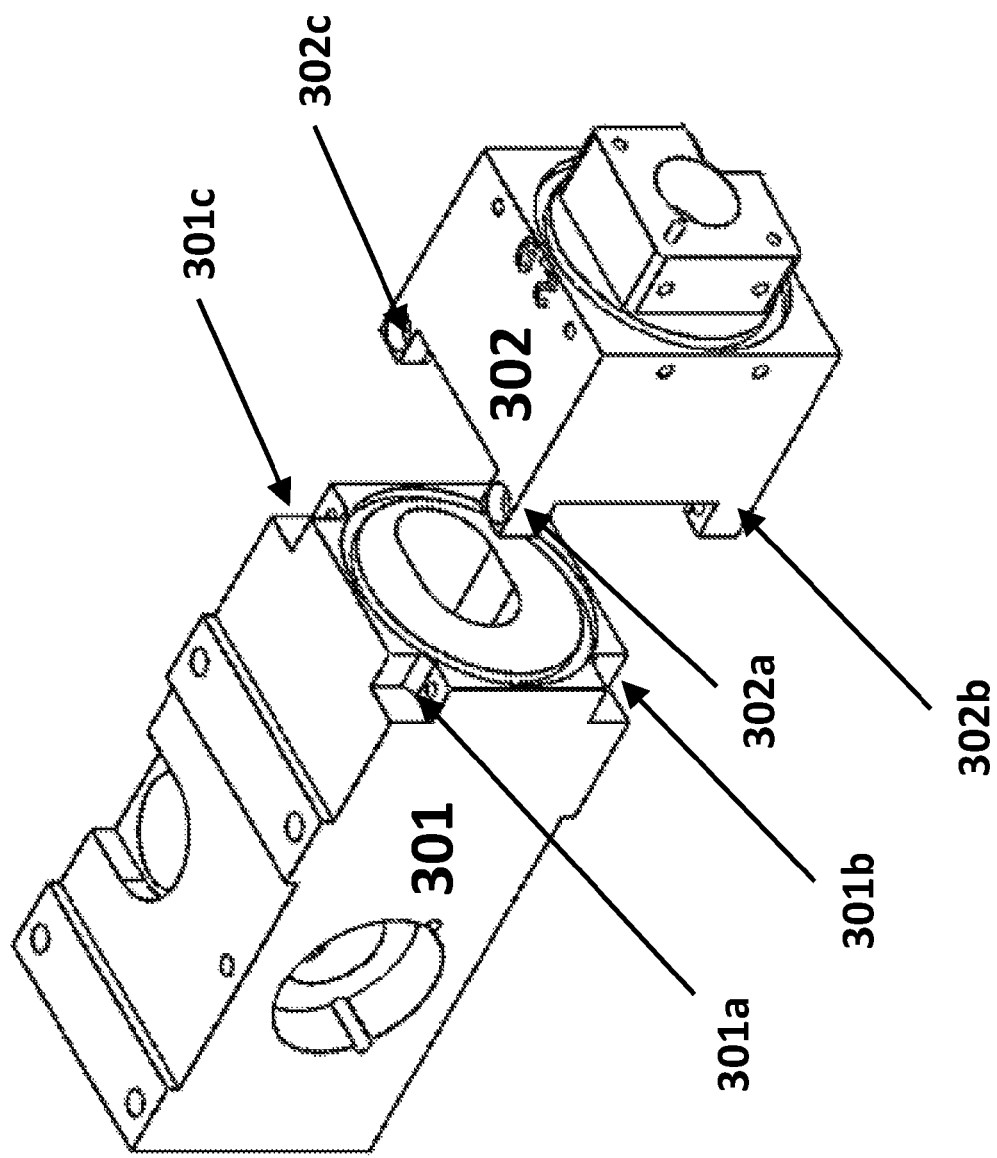
FIG. 3 depicts an exploded view of a mount coupled a connector according to certain embodiments of the present disclosure.

FIG. 3 depicts an exploded view of the mount that is coupled a connector according to certain embodiments of the present disclosure. As shown in FIG. 3, aligners 301a, 301b and 301c at the distal end of mount 301 are coupled with aligners 302a, 302b and 302c at the proximal end of the connector 302.

In embodiments, the distal end of the connector is configured to be coupled to one or more orifice plates. Depending on the light being collected, the connector may be configured to include one or more orifice plates, such as 2 or more, such as 3 or more, such as 5 or more and including 10 or more orifice plates. Each orifice plate includes one or more orifices (e.g., pinholes) that pass light from the connector to the optical collection component. For example, orifice plates of interest include 2 or more orifices, such as 3 or more orifices, such as 5 or more orifices, such as 7 or more orifices and including 10 or more orifices. In certain instances, the orifice plate includes 11 orifices.

The aperture of each orifice may be the same or different and may be any convenient shape, including but not limited to a circle, oval, rectangle, or other polygon. In certain instances, the pinhole is a circular aperture. The dimensions of each orifice in the orifice plate may vary, having a width (or diameter when in the shape of a circle) that ranges from 0.1 µm to 10 mm, such as from 0.5 µm to 9.5 mm, such as from 1 µm to 9 mm, such as from 5 µm to 8.5 mm, such as from 10 µm to 8 mm, such as from 25 µm to 7.5 mm, such as from 50 μm to 7 mm, such as from 100 μm to 6.5 mm, such as from 250 μm to 6 mm and including from 500 μm to 5.5 mm, for example 600 μm and 700 μm.

In certain embodiments, the orifice plate includes one or more slits. The slit aperture may be any convenient shape, including but not limited to an oval, rectangle or other polygon. In certain embodiments, the slit aperture is rectangular. The dimensions of the slit aperture may vary, having a length which ranges from 0.1 mm to 10 mm, such as from 1.25 mm to 9.5 mm, such as from 1.5 mm to 9 mm, such as from 2 mm to 8 mm, such as from 2.5 mm to 7 mm, such as from 3 mm to 6 mm and including from 3.5 mm to 5 mm. The width of the slit aperture may range from 1 μm to 1000 μm, such as from 2 μm to 900 μm, such as from 5 μm to 800 μm, such as from 10 μm to 700 μm, and including from 15 μm to 600 μm, for example a slit having an aperture width of 500 μm.

In some embodiments, the orifice plate has one or more reflective surfaces. The term "reflective" is used herein in its conventional sense to refer to the capability of the orifice plate to change the direction of an electromagnetic wave (e.g., by specular reflectance). All or part of the orifice plate may be reflective. For example, 10% or more of the orifice plate may be reflective, such as 25% or more, such as 50% or more, such as 75% or more, such as 90% or more and including 95% or more of the orifice plate may be reflective. In certain embodiments, the entire orifice plate is reflective (i.e., 100%). For example, the orifice plate may be a pinhole mirror. In certain instances, the pinhole mirror has one reflective surface. In other instances, the pinhole mirror has two reflective surfaces.

Depending on the size of the distal end of the connector, the dimensions of the orifice plate may vary, where in some instances the length of the orifice plate may range from 1 cm to 25 cm, such as from 2.5 cm to 45 cm, such as from 5 cm to 40 cm, such as from 7.5 cm to 35 cm and including from 10 cm to 25 cm and the width of the orifice plate may range from 1 cm to 50 cm, such as from 2.5 cm to 45 cm, such as from 5 cm to 40 cm, such as from 7.5 cm to 35 cm and including from 10 cm to 25 cm. Where the orifice plate is circular, the diameter may vary, in some embodiments, ranging from 1 cm to 10 cm, such as from 2 cm to 9 cm, such as from 3 cm to 8 cm and including from 4 cm to 7 cm. In some embodiments, the orifice plate is configured to have the same dimensions as the cross section of the connecter inner chamber. The thickness of the orifice plate may vary, ranging from 0.001 mm to 5 mm, such as from 0.005 mm to 4.5 mm, such as from 0.01 mm to 4 mm, such as from 0.05 mm to 3.5 mm, such as from 0.1 mm to 3 mm, such as from 0.5 mm to 2.5 mm and including from 1 mm to 2 mm.

In certain embodiments, the connector has a distal end that is configured to be coupled to one or more different types of optical collection systems (as described in greater detail below). In one example, the distal end of the connector is configured to be coupled to a fiber optics light relay system. In another example, the distal end of the connector is configured to be coupled to a free-space light relay system. Depending on the type of optical collection component, the distal end of the connector may be include one or more fasteners for attaching the distal end of the connector to the optical collection component, where suitable fasteners may include, but are not limited to magnets, latches, hinges, tethers, a screw thread or by one or more screws that secures the proximal end of the optical collection component to the distal end of the connector.

In some embodiments, the distal end of the connector includes an adapter for coupling the orifice plate to the connector. In some instances, the adapter is releasably attached to the distal end of the connector, such with a non-permanent adhesive or screw threaded with the inner chamber of the connector. In other instances, the adapter is permanently incorporated into the distal end of the connector, such as with a permanent adhesive or is molded directly into the distal end of the connector.

The orifice plate may be coupled to the distal end of the connector or adapter with any suitable fastening protocol, such as with one or more magnets, adhesive (e.g., permanent or non-permanent), placed into a slot on the adapter, screw threaded or a combination there. In certain instances, the orifice plate is fastened to the connector by one or more screws that connects the corners of the orifice plate to the corners at the distal end of the connector.

In some embodiments, the distal end of the connector may also include one or more optical adjustment protocols. By "optical adjustment" is meant that light conveyed through the connector from the mount is changed as desired before being conveyed to the orifice plate. For example, the optical adjustment may be to focus the conveyed beam of light onto the surface of a orifice plate, increase the dimensions of the conveyed beam of light, or to collimate the beam of light. In some instances, optical adjustment is a magnification protocol so as to increase the beam spot produced by the conveyed light, such as increasing beam spot by 5% or greater, such as by 10% or greater, such as by 25% or greater, such as by 50% or greater and including increasing the dimensions of the beam spot by 75% or greater. In other embodiments, optical adjustment includes focusing the conveyed light so as to reduce the dimensions of the beam spot, such as by % or greater, such as by 10% or greater, such as by 25% or greater, such as by 50% or greater and including reducing the dimensions of the beam spot by 75% or greater.

In certain embodiments, optical adjustment includes collimating the conveyed light. The term "collimate" is used in its conventional sense to refer to the optically adjusting the co-linearity of light propagation or reducing divergence by the light of from a common axis of propagation. In some instances, collimating includes narrowing the spatial cross section of a light beam.

Optical adjustment components may be any convenient device or structure which provides the desired change in the conveyed light in the connector and may include, but is not limited to, lenses, mirrors, pinholes, slits, gratings, light refractors, and any combinations thereof. The connector may include one or more optical adjustment components as needed, such as 2 or more, such as 3 or more, such as 4 or more and including 5 or more optical adjustment components. In some embodiments, the connector and the optical adjustment component are releasably coupled together, such as being screwed threaded or coupled together with an adhesive. In other embodiments, the optical adjustment component is non-releasably attached to the connector, such as with a permanent adhesive, co-molded together or integrated into the connector.

In some embodiments, the optical adjustment component is a focusing lens having a magnification ratio of from 0.1 to 0.95, such as a magnification ratio of from 0.2 to 0.9, such as a magnification ratio of from 0.3 to 0.85, such as a magnification ratio of from 0.35 to 0.8, such as a magnification ratio of from 0.5 to 0.75 and including a magnification ratio of from 0.55 to 0.7, for example a magnification ratio of 0.6. For example, the focusing lens is, in certain instances, a double achromatic de-magnifying lens having a magnification ratio of about 0.6. The focal length of the focusing lens may vary, ranging from 5 mm to 20 mm, such as from 6 mm to 19 mm, such as from 7 mm to 18 mm, such as from 8 mm to 17 mm, such as from 9 mm to 16 and including a focal length ranging from 10 mm to 15 mm. In certain embodiments, the focusing lens has a focal length of about 10 mm.

In other embodiments, the optical adjustment component is a collimator. The collimator may be any convenient collimating protocol, such as one or more mirrors or curved lenses or a combination thereof. For example, the collimator is in certain instances a single collimating lens. In other instances, the collimator is a collimating mirror. In yet other instances, the collimator includes two lenses. In still other instances, the collimator includes a mirror and a lens. Where the collimator includes one or more lenses, the focal length of the collimating lens may vary, ranging from 5 mm to 40 mm, such as from 6 mm to 37.5 mm, such as from 7 mm to 35 mm, such as from 8 mm to 32.5 mm, such as from 9 mm to 30 mm, such as from 10 mm to 27.5 mm, such as from 12.5 mm to 25 mm and including a focal length ranging from 15 mm to 20 mm.

In certain embodiments, the optical adjustment component is a wavelength separator. The term "wavelength separator" is used herein in its conventional sense to refer to an optical protocol for separating polychromatic light into its component wavelengths for detection. Wavelength separation, according to certain embodiments, may include selectively passing or blocking specific wavelengths or wavelength ranges of the polychromatic light. Wavelength separation protocols of interest which may be a part of or combined with the subject connector, include but are not limited to, colored glass, bandpass filters, interference filters, dichroic mirrors, diffraction gratings, monochromators and combinations thereof, among other wavelength separating protocols.

The connector may include one or more wavelength separators, such as two or more, such as three or more, such as four or more, such as five or more and including 10 or more wavelength separators. Where systems include two or more wavelength separators, the wavelength separators may be utilized individually or in series to separate polychromatic light into component wavelengths. In some embodiments, wavelength separators are arranged in series. In other embodiments, wavelength separators are arranged individually such that one or more measurements are conducted to collect the light using each of the wavelength separators.

In some embodiments, the connector includes one or more optical filters, such as a bandpass filter having minimum bandwidths ranging from 2 nm to 100 nm, such as from 3 nm to 95 nm, such as from 5 nm to 95 nm, such as from 10 nm to 90 nm, such as from 12 nm to 85 nm, such as from 15 nm to 80 nm and including bandpass filters having minimum bandwidths ranging from 20 nm to 50 nm.

In embodiments, the mount and connector are configured to be coupled to and in optical alignment with optical collection component. The optical collection component may be any suitable light collection protocol that collects light conveyed through the mount and connector and directs the light to a detector. In some embodiments, the optical collection component includes a fiber optics light relay system. In other embodiments, the optical collection component is a free-space light relay system.

In embodiments, the optical collection component may be physically coupled to the distal end of the connector, such as with an adhesive, co-molded together or integrated into the connector. In certain embodiments, the optical collection component and connector are integrated into a single unit. In some instances, the optical collection component is coupled to the orifice plate and the distal end of the connector. In certain instances, the optical collection component is coupled to the orifice plate and the distal end of the connector with an adapter that fastens the optical collection component and orifice plate to the distal end of the connector with one or more screws at the outer edges.

In other embodiments, the distal end of the connector and the optical collection component are in optical communication, but are not physically in contact. In embodiments, the optical collection component may be positioned 0.001 mm or more from the distal end of connector, such as 0.005 mm or more, such as 0.01 mm or more, such as 0.05 mm or more, such as 0.1 mm or more, such as 0.5 mm or more, such as 1 mm or more, such as 10 mm or more, such as 25 mm or more, such as 50 mm or more and including 100 mm or more from the distal end of the connector.

In certain embodiments, the optical collection component is a fiber optics light relay system and light conveyed through the mount and connector are directed onto the surface of a fiber optics light relay bundle. Any fiber optics light relay system may be employed to propagate light conveyed through the connector onto the active surface of a detector. In certain embodiments, suitable fiber optics light relay systems for propagating light from the connector to a detector include, but are not limited to, fiber optics light relay systems such as those described in U.S. Pat. No. 6,809,804, the disclosure of which is herein incorporated by reference.

Figure 4:
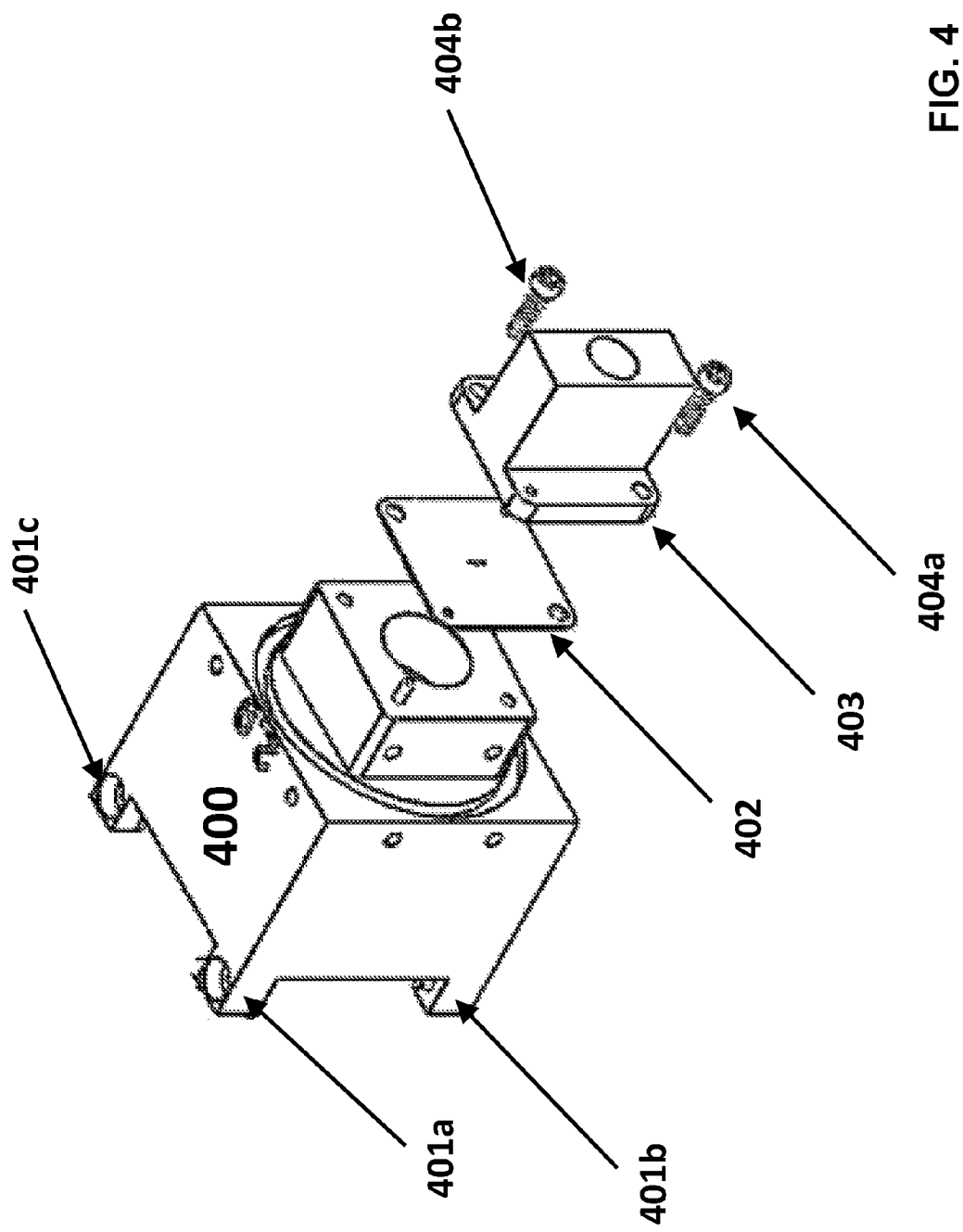
FIG. 4 depicts an exploded view of a connector coupled to the bundle head of a fiber optics light relay system according to certain embodiments of the present disclosure.

FIG. 4 depicts an exploded view of a connector that is coupled to the bundle head of a fiber optics light relay system according to certain embodiments of the present disclosure. Connector 400 includes a proximal end and a distal end, where the proximal end includes aligners 401a, 401b and 401c which couple to aligners at the distal end of the mount. Connector 400 also includes a distal end that is coupled to orifice plate 402 and the bundle head of fiber optics light relay system 403 through screws 404a and 404b which physically couple fiber optics light relay system 403 and orifice plate 402 to the distal end of connector 400.

In other embodiments, the optical collection component is a free-space light relay system. The phrase "free-space light relay" is used herein in its conventional sense to refer to light propagation that employs a configuration of one or more optical components to direct light to a detector through free-space. In certain embodiments, the free-space light relay system includes a housing having a proximal end and a distal end, the proximal end being coupled to the orifice plate and the distal end of the connector. The free-space relay system may include any combination of different optical adjustment components, such as one or more of lenses, mirrors, slits, pinholes, wavelength separators, or a combination thereof. For example, in some embodiments, free-space light relay systems of interest include one or more focusing lens. In other embodiments, the subject free-space light relay systems include one or more mirrors. In yet other embodiments, the free-space light relay system includes a collimating lens. In certain embodiments, suitable free-space light relay systems for propagating light from the connector to a detector include, but are not limited to, light relay systems such as those described in U.S. Pat. Nos. 7,643,142; 7,728,974 and 8,223,445, the disclosures of which is herein incorporated by reference.

Figure 5:
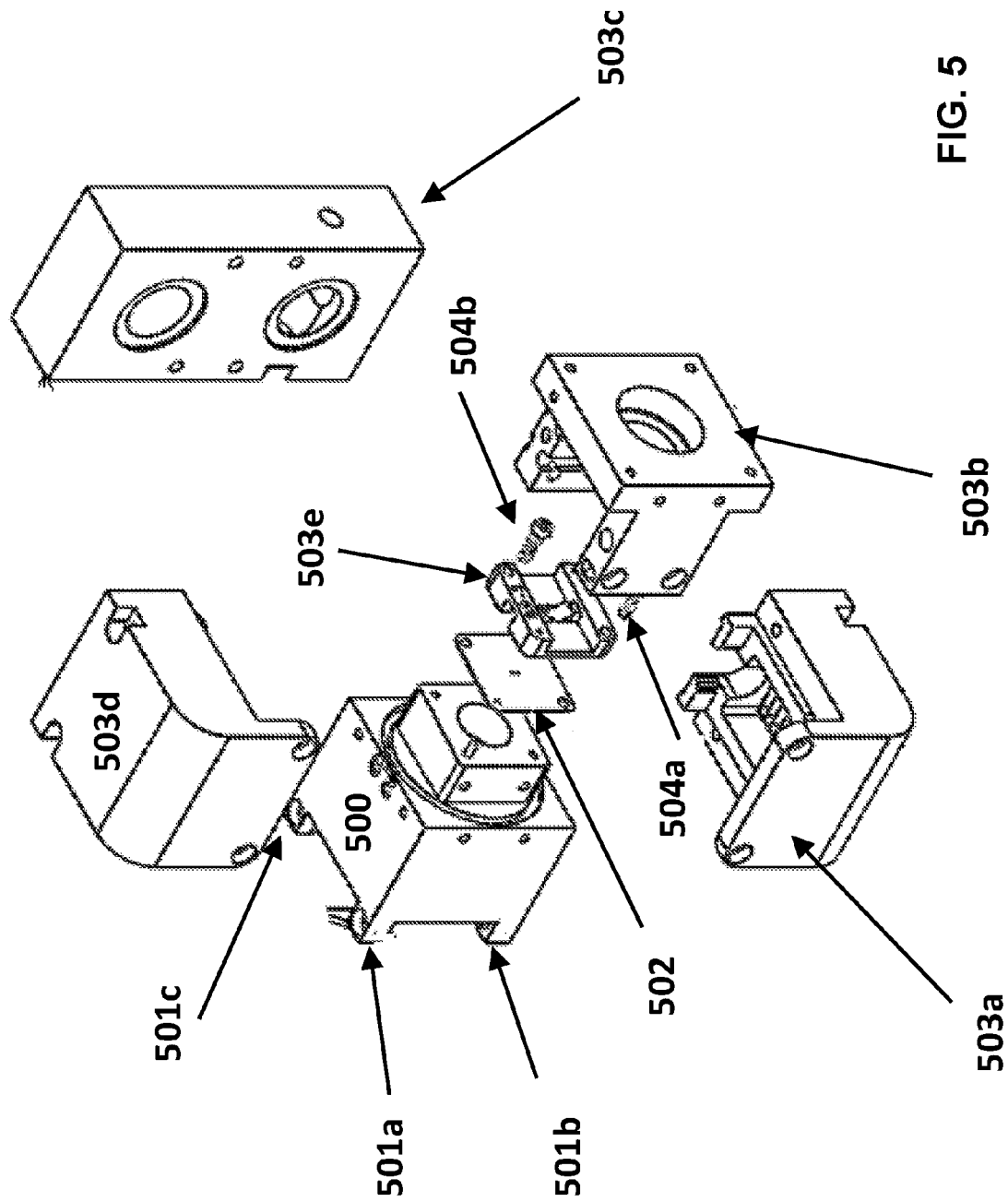
FIG. 5 depicts an exploded view of a connector that is coupled to a free-space light relay system according to certain embodiments of the present disclosure.

FIG. 5 depicts an exploded view of a connector that is coupled to a free-space light relay system according to certain embodiments of the present disclosure. Connector 500 includes a proximal end and a distal end, where the proximal end includes aligners 501a, 501b and 501c which couple to aligners at the distal end of the mount. Connector 500 also includes a distal end that is coupled to orifice plate 502 and the proximal end of a free-space light relay 503 system that is collectively composed of parts 503*a-e* through screws 504*a* and 504*b*, which physically couples the proximal end of free-space light relay system 503 and orifice plate 502 to the distal end of connector 500.

As discussed in greater detail below, the subject optically aligned light collection systems are configured to maintain optical alignment of the two or more releasably attachable components (i.e., mount and connector). In embodiments, the subject optically aligned light collection systems are configured to maintain optical alignment, as desired, such as until one or more components are deliberately and physically detached from the other component. For example, the subject optically aligned light collection systems are configured to maintain optical alignment of the two components for a duration of 1 hour or longer, such as 4 hours or longer, such as 6 hours or longer, such as 12 hours or longer, such as 18 hours or longer, such as 24 hours or longer, such as 3 days or longer, such as 7 days or longer, such as 2 weeks or longer and including for 1 month or longer.

Methods for Assembling Optically Aligned Components of a Light Collection System As summarized above, aspects of the disclosure also include methods for assembling components of the optically aligned light collection system. In some embodiments, the subject methods include coupling a connector to a mount by connecting a first aligner at the proximal end of the connector to a second aligner at the distal end of the mount, attaching an orifice plate to the distal end of the connector and coupling an optical collection system to the distal end of the connector, such that connecting the first aligner and the second aligner is sufficient to optically align the mount and connecter with the orifice plate and optical collection system. As described above, the phrase "optically aligned" is used herein its conventional sense to refer to two or more optical components being positioned in line with each other such that the components have the same optical axis (i.e., are optically concentric). For example, optically aligned light collection systems according to embodiments of the present disclosure include a mount and a connector where the optical center of the mount is displaced from the optical center of the connector by 100 μm or less when measured orthogonally to the optical axis, such as 50 μm or less, such as 25 μm or less, such as 15 μm or less, such as 10 μm or less, such as 5 μm or less, such 2 μm or less, such as 1 μm or less, such as 0.5 μm or less, such as 0.1 μm or less, such as 0.05 μm or less, such as 0.01 μm or less, such as 0.005 μm or less and including where the optical center of the mount is displaced from the optical center of the connector by 0.001 μm or less when measured orthogonally to the optical axis. As described in greater detail below, after coupling an aligner at the distal end of the mount to an aligner at the proximal end of the connector, the optical center of a mount is displaced from the optical center of a connector by 100 μm or less when measured orthogonally to the optical axis, such as 50 μm or less, such as 25 μm or less, such as 15 μm or less, such as 10 μm or less, such as 5 μm or less, such 2 μm or less, such as 1 μm or less, such as 0.5 μm or less, such as 0.1 μm or less, such as 0.05 μm or less, such as 0.01 μm or less, such as 0.005 μm or less and including by 0.001 μm or less when measured orthogonally to the optical axis.

In practicing the subject methods according to certain embodiments, the mount is aligned with the connector by coupling one or more aligners positioned at the distal end of the mount to one or more aligners positioned at the proximal end of the connector. By "coupling" is meant that the aligners at the proximal end of the connector are brought into contact (e.g., press-fitted) with the aligners positioned at the distal end of the mount. As described above, the mount and connector may include any number of aligners, such as 2 or more aligners, such as 3 or more aligners, such as 4 or more aligners, such as 5 or more aligners, such as 7 or more aligners and including 10 or more aligners. In embodiments, each aligner at the proximal end of the mount is coupled to a complimentary aligner at the distal end of the connector. Accordingly, optically aligning the mount and connector may include coupling 2 or more aligners together, such as 3 or more aligners, such as 4 or more aligners, such as 5 or more aligners and including coupling 10 or more aligners together.

Depending on the type of aligner on the distal end of the mount and the proximal end of the connector, coupling the mount to the connector may vary. In some embodiments, the distal end of the connector includes one or more alignment protrusions (e.g., 4 or more polygonal-shaped press-fit dowels) and the proximal end of the connector includes one or more alignment recesses (e.g., 4 or more polygonal-shaped notches). In these embodiments, coupling the distal end of the mount to the proximal end of the mount includes inserting each of the alignment protrusions of the mount into the alignment recesses of the connector.

For example, where an aligner at the proximal end of the connector is an alignment protrusion (e.g., press-fit dowel), and the aligner at the distal end of the mount is an alignment recess, methods may include inserting the protrusion of the connector into the recess of the mount such that the outer surfaces of the protrusion are spaced apart from the inner walls of the recess by 100 μm or less, such as 50 μm or less, such as 25 μm or less, such as 15 μm or less, such as 10 μm or less, such as 5 μm or less, such 2 μm or less, such as 1 μm or less, such as 0.5 μm or less, such as 0.1 μm or less, such as 0.05 μm or less, such as 0.01 μm or less, such as 0.005 μm or less and including by 0.001 μm. In certain instances, methods include inserting the protrusion of the connector into the recess of the mount such that the outer surfaces of the protrusion are in contact the inner walls of the recess. In some embodiments, methods include inserting the protrusion into the recess such that the top surface of the protrusion is spaced apart from the bottom wall of the recess by 100 μm or less, such as 50 μm or less, such as 25 μm or less, such as 15 μm or less, such as 10 μm or less, such as 5 μm or less, such 2 μm or less, such as 1 μm or less, such as 0.5 μm or less, such as 0.1 μm or less, such as 0.05 μm or less, such as 0.01 μm or less, such as 0.005 μm or less and including by 0.001 μm or less. In certain instances, the protrusion is inserted into the recess such that the top surface of the protrusion is in contact with the bottom wall of the recess and the outer side surfaces of the protrusion are in contact with the inner walls of the recess.

In other embodiments, methods include inserting one or more protrusions on the mount into one or more recesses on the connector. For example, protrusions on the mount may be inserted into recesses on the connector such that the outer surfaces of the protrusion are spaced apart from the inner walls of the recess by 100 μm or less, such as 50 μm or less, such as 25 μm or less, such as 15 μm or less, such as 10 μm or less, such as 5 μm or less, such 2 μm or less, such as 1 μm or less, such as 0.5 μm or less, such as 0.1 μm or less, such as 0.05 μm or less, such as 0.01 μm or less, such as 0.005 μm or less and including by 0.001 μm. In certain instances, methods include inserting the protrusion of the mount into the recess of the connector such that the outer surfaces of the protrusion are in contact the inner walls of the recess. In still other embodiments, methods include inserting the protrusions of the mount into the recesses of the connector such that the top surface of the protrusion is spaced apart from the bottom wall of the recess by 100 µm or less, such as 50 µm or less, such as 25 µm or less, such as 15 µm or less, such as 10 µm or less, such as 5 µm or less, such 2 µm or less, such as 1 µm or less, such as 0.5 µm or less, such as 0.1 µm or less, such as 0.05 µm or less, such as 0.01 µm or less, such as 0.005 µm or less and including by 0.001 µm or less. In certain instances, the protrusions of the mount are inserted into the recesses of the connector such that the top surface of the protrusion is in contact with the bottom wall of the recess and the outer side surfaces of the protrusion are in contact with the inner walls of the recess.

In certain embodiments, the mount and connector have a polygonal cross-sectional shape and each of the aligners is identical and positioned at the edge corners of the mount and the connector. In these embodiments, the mount and the connector may be non-orientation specific and may be coupled together in a plurality of different rotational orientations. For example, in some instances the mount and connector have a square-shaped cross section and each of the aligners are positioned at the four corners at the distal end of the mount and at the four corners at the proximal end of the connector.

In other embodiments, both the proximal end of the connector and the distal end of the mount include one or more alignment protrusions and one or more alignment recesses. In these embodiments, coupling the proximal end of the connector to the distal end of the mount includes inserting the alignment protrusions of the connector into the alignment recesses in the mount and inserting the alignment protrusions of the mount into the alignment recesses of the connector.

In some embodiments, the mount is releasably coupled to the connector. In these embodiments, the connector may be freely detached and re-attached to the mount. In certain instances, methods include detaching a first connector that is releasably attached to the mount and coupling a second connector to the mount. In some embodiments, one or more of the connector and the mount may include a fastener for coupling the connector to mount. Suitable fasteners may include, but are not limited to, hook and loop fasteners, magnets, latches, notches, countersinks, counter-bores, grooves, pins, tethers, hinges, Velcro, non-permanent adhesives or a combination thereof.

In certain embodiments, the distal end of the mount may include one or more magnets for coupling to one or more magnets at the proximal end of the connector. In practicing the subject methods in these embodiments, alignment between the mount and connector may be achieved by coupling the magnets at the distal end of the mount with the magnets at the proximal end of the connector. In certain embodiments, the mount and connector include both aligners and magnets. The term "magnet" is used herein in its conventional sense to refer to a magnetic material that has a persistent magnetic field such that the magnetic field from the magnet does not substantially decrease over time. For example, the magnet may be an iron alloy material having aluminum, nickel and cobalt (i.e., Alnico magnets), a ceramic or ferrite magnet, a rare-earth magnet such as samarium-cobalt magnets (e.g., $SmCo_5$), neodymium alloy (NdFeB) magnets (e.g., $Nd_2Fe_{14}B$) or a combination thereof. Depending on the size of the magnet, the magnet field produced by magnets of interest positioned at the connector proximal end range from 0.01 T to 10 T, or from 0.01 T to 5 T, or from 0.01 T to 2 T, or from 0.1 T to 2 T, or from 0.1 T to 1.5 T, including from 0.1 T to 1 T.

Where the distal end of the mount and proximal end of the connector include one or more magnets, the magnets at the proximal end of the connector are placed into physical contact with the magnets positioned at the distal end of the mount to couple the mount and connector together. In certain embodiments, the magnets positioned at the proximal end of the mount and the distal end of the connector are disk shaped and alignment of the mount and connector is achieved when each magnet of the connector is concentric (i.e., centered) with each coupled magnet of the mount. For example, in certain instances the connector and the mount are optically aligned when the center of each magnet on connector is displaced from the center of each coupled magnet on the mount by 100 µm or less, such as 50 µm or less, such as 25 µm or less, such as 15 µm or less, such as 10 µm or less, such as 5 µm or less, such 2 µm or less, such as 1 µm or less, such as 0.5 µm or less, such as 0.1 µm or less, such as 0.05 µm or less, such as 0.01 µm or less, such as 0.005 µm or less and including by 0.001 µm or less.

By placing the magnets of the connector into contact with the magnets of the mount, the connector is aligned and releasably attached to the mount by the magnetic attraction between each set of magnet contacts. In some embodiments, coupling of the magnets of the connector to the magnets of the mount maintains optical alignment of the connector with the mount for a period of time, as desired, such as until the connector is deliberately and physically detached from the mount. For example, coupling of the magnets of the connector to the magnets of the mount maintains optical alignment of the connector and the mount for 1 hour or longer, such as 4 hours or longer, such as 6 hours or longer, such as 12 hours or longer, such as 18 hours or longer, such as 24 hours or longer, such as 3 days or longer, such as 7 days or longer, such as 2 weeks or longer and including for 1 month or longer.

In certain embodiments, the magnets are positioned at the edge corners of the mount and the connector, such where the mount and connector have a square cross-sectional shape and magnets are positioned at each of the four corners of the distal end of the mount and the proximal end of the connector. In these embodiments, the mount and the connector may be non-orientation specific and may be coupled together in a plurality of different rotational orientations.

In certain embodiments, the mount is permanently integrated into a flow cytometer and methods include coupling the connector to the mount within the flow cytometer. In these embodiments, methods include coupling the aligners positioned at the proximal end of the connector with the aligners positioned at the distal end of a mount that is fixed within the flow cytometer. By coupling the aligners at the proximal end of the connector with the aligners at the distal end of the mount, the connector is placed into optical alignment with the mount in the flow cytometer.

In certain embodiments, methods include separating the connector from the mount. By "separating" is meant that the connector is not in any physical contact with the mount. For example, in some instances each of the aligners of the connector are removed from contact with the aligners of the mount. In other instances, the connector is separated from the mount by removing each of the magnets of the connector from contact with the magnets of the mount. In practicing the subject methods, a second connector may be coupled to the mount after a first connector is separated. In these embodiments, the first connector is separated from the mount by disconnecting each of the aligners (or magnets)

between the mount and connector and aligners of the second connector are fitted into position with aligners of the mount.

As summarized above, by coupling the aligners of the mount with the aligners of the connector, the mount and connector are placed into optical alignment with each other and with an orifice plate and optical collection component coupled to the connector (as described in greater detail below). As such, when a first connector is separated and replaced with a second connector, fitting the aligners of the second connector with the aligners of the mount is sufficient, in these embodiments, to align the mount with the second connector and with pinholes and the optical collection component coupled to the second connector. In embodiments, no added alignments steps are required to align the mount with the connector once the aligners of the connector and the mount are fitted into position.

In some embodiments, methods also include coupling an orifice plate to the distal end of the connector. One or more orifice plates may be coupled to the connector, such as 2 or more, such as 3 or more, such as 5 or more and including 10 or more orifice plates. Each orifice plate may include one or more orifices (i.e., pinholes) that pass light from the connector to the optical collection component. For example, orifice plates of interest include 2 or more orifices, such as 3 or more orifices, such as 5 or more orifices, such as 7 or more orifices, such as 10 or more orifices, such as 11 orifices. In embodiments, coupling the orifice plate to the distal end of the connector is sufficient to place the orifice plate in optical alignment with the mount and connector.

In certain embodiments, the orifice plate includes one or more slits. The slit aperture may be any convenient shape, including but not limited to an oval, rectangle or other polygon. In certain embodiments, the slit aperture is rectangular. The dimensions of the slit aperture may vary, having a length which ranges from 0.1 mm to 10 mm, such as from 1.25 mm to 9.5 mm, such as from 1.5 mm to 9 mm, such as from 2 mm to 8 mm, such as from 2.5 mm to 7 mm, such as from 3 mm to 6 mm and including from 3.5 mm to 5 mm. The width of the slit aperture may range from 1 μm to 1000 μm, such as from 2 μm to 900 μm, such as from 5 μm to 800 μm, such as from 10 μm to 700 μm, and including from 15 μm to 600 μm, for example a slit having an aperture width of 500 μm.

In some embodiments, the orifice plate has one or more reflective surfaces. All or part of the orifice plate may be reflective. For example, 10% or more of the orifice plate may be reflective, such as 25% or more, such as 50% or more, such as 75% or more, such as 90% or more and including 95% or more of the orifice plate may be reflective. In certain embodiments, the entire orifice plate is reflective (i.e., 100%). For example, the orifice plate may be a pinhole mirror. In certain instances, the pinhole mirror has one reflective surface. In other instances, the pinhole mirror has two reflective surfaces.

In certain instances, the orifice plate is attached to an adapter at the distal end of the connector. For example, the adapter may be a releasably attachable component that couples to the distal end of the connector and is configured for attaching to the orifice plate. In other instances, the adapter is permanently incorporated into the distal end of the connector, such as with a permanent adhesive or is molded directly into the distal end of the connector.

The orifice plate may be coupled to the distal end of the connector or adapter with any suitable fastening protocol, such as with one or more magnets, adhesive (e.g., permanent or non-permanent), placed into a slot on the adapter, screw threaded or a combination there. In certain instances, the orifice plate is fastened to the distal end of the connector with one or more screws at the outer edges of the orifice plate.

In certain embodiments, methods also include coupling the distal end of the connector to an optical collection component. For example, the distal end of the connector may be coupled to the optical collection component by one or more screws that are screw threaded into the edge corners of the connector distal end. In some instances, the orifice plate is coupled to the distal end of the connector concurrently while coupling the optical collection component, such as with one or more screws which couple the optical collection component, orifice plate and distal end of the connector. In embodiments, coupling the optical collection component to the distal end of the connector is sufficient to place the optical collection component in optical alignment with the mount and connector.

As discussed above, the optical collection component may be a fiber optics light relay system or a free-space light relay system. In some embodiments, the optical collection component is a fiber optics light relay system and methods include coupling the bundle head of the fiber optics light relay system to the distal end of the connector. Any suitable fiber optics light relay system may be employed to propagate light conveyed through the connector onto the active surface of a detector, where suitable fiber optics light relay systems may include, but are not limited to, those described in U.S. Pat. No. 6,809,804, the disclosure of which is herein incorporated by reference.

Figure 6:
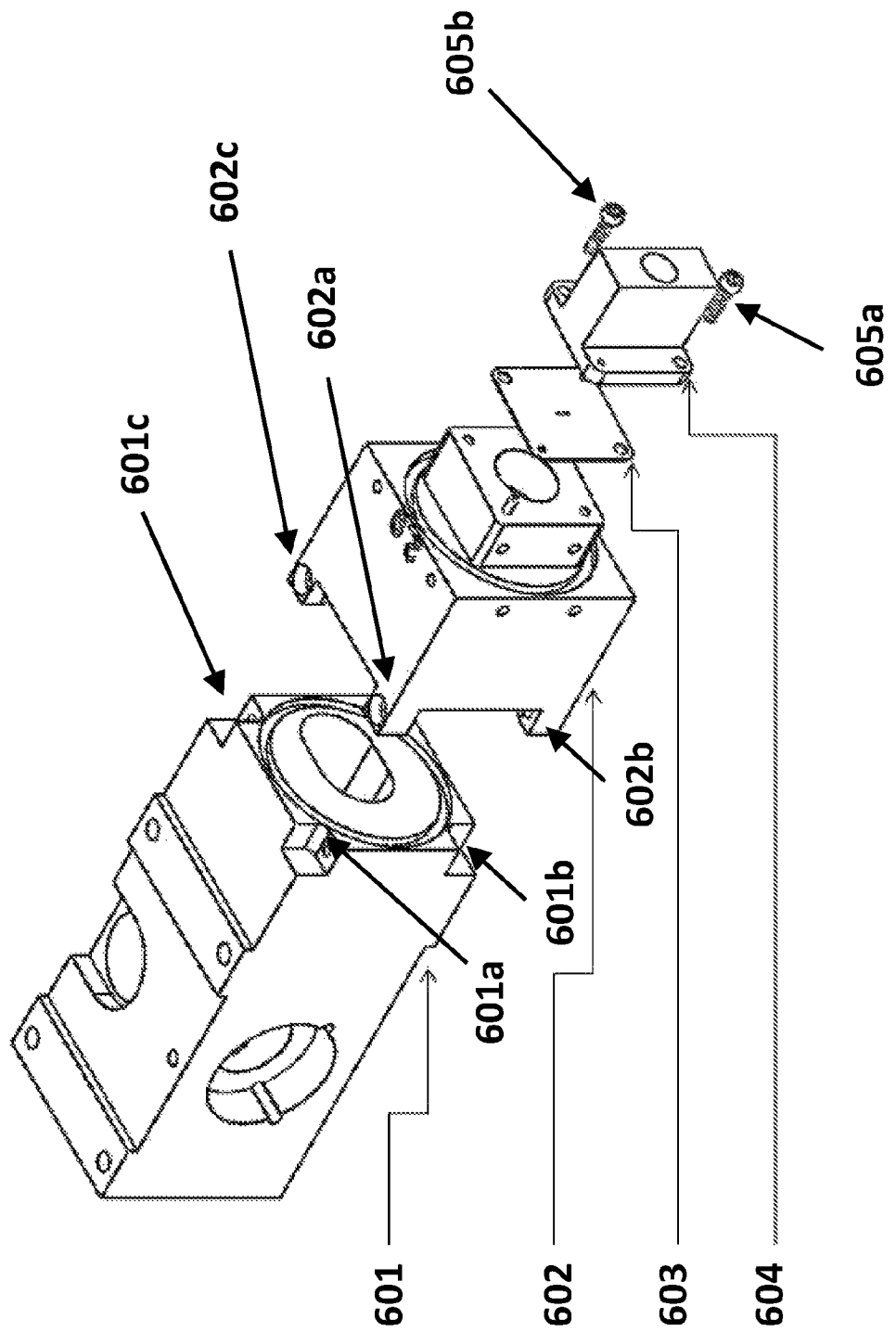
FIG. 6 depicts an exploded view of optically aligned light collection systems coupled to an orifice plate and a fiber optics light relay system according to certain embodiments of the present disclosure.

FIG. 6 depicts an exploded view of optically aligned light collection systems coupled to an orifice plate and a fiber optics light relay system according to certain embodiments of the present disclosure. FIG. 6 shows mount 601 and connector 602 coupled through alignment recesses 601a, 601b and 601c at the distal end of mount 601 and alignment protrusions 602a, 602b and 602c at the proximal end of connector 602. The distal end of connector 602 is coupled to orifice plate 603 and the bundle head of fiber optics light relay system 604 with screws 605a and 605b.

In other embodiments, the optical collection component is a free-space light relay system and methods include coupling the distal end of the connector to the proximal end of a free-space relay system housing. Any suitable free-space light relay system may be employed to propagate light from the connector to the active surface of a detector, where suitable free-space light relay systems may include, but are not limited to, those described in U.S. Pat. Nos. 7,643,142; 7,728,974 and 8,223,445, the disclosures of which is herein incorporated by reference.

Figure 7:
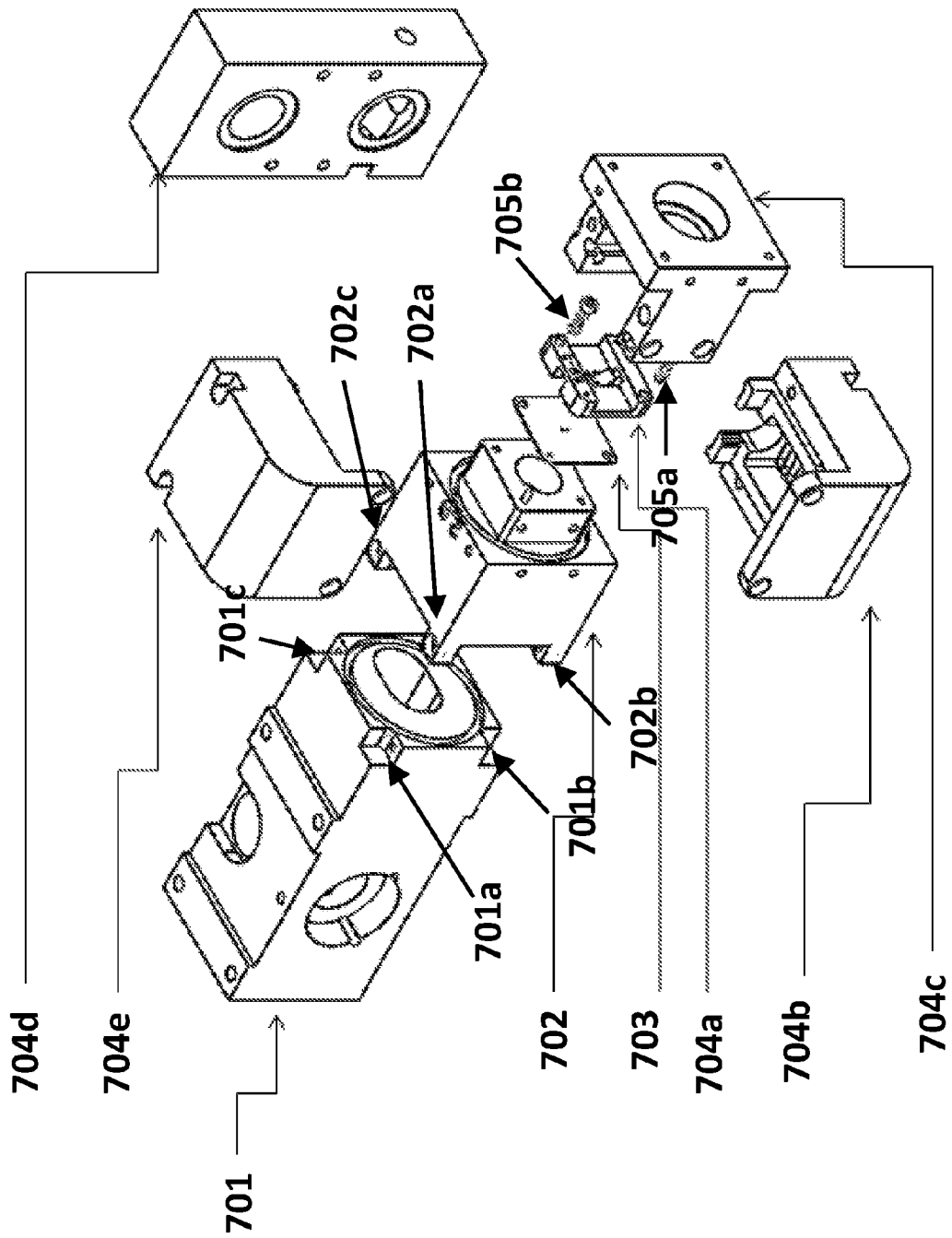
FIG. 7 depicts an exploded view of optically aligned light collection systems coupled to an orifice plate and a free-space light relay system according to certain embodiments of the present disclosure.

FIG. 7 depicts an exploded view of optically aligned light collection systems coupled to an orifice plate and a free-space light relay system according to certain embodiments of the present disclosure. FIG. 7 shows mount 701 and connector 702 coupled through alignment recesses 701a, 701b and 701c at the distal end of mount 701 and alignment protrusions 702a, 702b and 702c at the proximal end of connector 702. The distal end of connector 702 is coupled to orifice plate 703 and the proximal end of a free-space light relay system 704 (collectively composed of components 704a-e) with screws 705a and 705b.

Systems for Measuring Light Emitted by a Sample

Aspects of the present disclosure also include systems for measuring light from a sample (e.g., in the flow stream in a flow cytometer). In certain embodiments, systems include a light source, one or more detectors or a detector array and one or more of the subject optically aligned light collection systems for collecting light emitted by the sample, as described above. For example, systems of interest may include a light source, one or more detectors or a detector array and an optically aligned light collection system (as described above) that includes: a mount having an orifice for receiving light (e.g., from a flow stream in a flow cytometer), an adapter configured to couple to a camera, a fastener for attaching a lens and an aligner positioned at the distal end of the mount for coupling to and maintaining optical alignment with a connector and a connector that is configured to be coupled to an orifice plate and is coupled to the mount through the aligners. In some embodiments, the system is a flow cytometer. In some instances, the mount is non-releasably integrated into the flow cytometer. In certain embodiments, the mount and connector are optically aligned with an orifice plate and optical collection component (e.g., fiber optics or free-space light relay system).

Systems of interest for measuring light from a sample include a light source. In embodiments, the light source may be any suitable broadband or narrow band source of light. Depending on the components in the sample (e.g., cells, beads, non-cellular particles, etc.), the light source may be configured to emit wavelengths of light that vary, ranging from 200 nm to 1500 nm, such as from 250 nm to 1250 nm, such as from 300 nm to 1000 nm, such as from 350 nm to 900 nm and including from 400 nm to 800 nm. For example, the light source may include a broadband light source emitting light having wavelengths from 200 nm to 900 nm. In other instances, the light source includes a narrow band light source emitting a wavelength ranging from 200 nm to 900 nm. For example, the light source may be a narrow band LED (1 nm-25 nm) emitting light having a wavelength ranging between 200 nm to 900 nm. In some embodiments, the light source is a laser, such as continuous wave laser. For example, the laser may be a helium-neon (HeNe) laser. In certain embodiments, the light source is a laser in a flow cytometer.

In other embodiments, the light source is a non-laser light source, such as a lamp, including but not limited to a halogen lamp, deuterium arc lamp, xenon arc lamp, a light-emitting diode, such as a broadband LED with continuous spectrum, superluminescent emitting diode, semiconductor light emitting diode, wide spectrum LED white light source, an multi-LED integrated. In some instances the non-laser light source is a stabilized fiber-coupled broadband light source, white light source, among other light sources or any combination thereof.

The light source may be positioned any suitable distance from the sample (e.g., the flow stream in a flow cytometer), such as at a distance of 0.001 mm or more from the flow stream, such as 0.005 mm or more, such as 0.01 mm or more, such as 0.05 mm or more, such as 0.1 mm or more, such as 0.5 mm or more, such as 1 mm or more, such as 5 mm or more, such as 10 mm or more, such as 25 mm or more and including at a distance of 100 mm or. In addition, the light source irradiate the sample at any suitable angle (e.g., relative the vertical axis of the flow stream), such as at an angle ranging from 10° to 90°, such as from 15° to 85°, such as from 20° to 80°, such as from 25° to 75° and including from 30° to 60°, for example at a 90° angle.

The light source may be configured to irradiate the sample continuously or in discrete intervals. In some instances, systems include a light source that is configured to irradiate the sample continuously, such as with a continuous wave laser that continuously irradiates the flow stream at the interrogation point in a flow cytometer. In other instances, systems of interest include a light source that is configured to irradiate the sample at discrete intervals, such as every 0.001 milliseconds, every 0.01 milliseconds, every 0.1 milliseconds, every 1 millisecond, every 10 milliseconds, every 100 milliseconds and including every 1000 milliseconds, or some other interval. Where the light source is configured to irradiate the sample at discrete intervals, systems may include one or more additional components to provide for intermittent irradiation of the sample with the light source. For example, the subject systems in these embodiments may include one or more laser beam choppers, manually or computer controlled beam stops for blocking and exposing the sample to the light source.

In some embodiments, light emitted by the sample is propagated through the optically aligned mount and connector light collection system and collected by an optical collection system (as described above) which conveys the collected light to a detector. Detectors of interest may include, but are not limited to optical sensors or photodetectors, such as active-pixel sensors (APSs), avalanche photodiode, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, the collected light is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors. In some embodiments, the imaging sensor is a CCD camera. For example, the camera may be an electron multiplying CCD (EMCCD) camera or an intensified CCD (ICCD) camera. In other embodiments, the imaging sensor is a CMOS-type camera. Where the collected light is measured with a CCD, the active detecting surface area of the CCD may vary, such as from $0.01$ cm$^2$ to $10$ cm$^2$, such as from $0.05$ cm$^2$ to $9$ cm$^2$, such as from, such as from $0.1$ cm$^2$ to $8$ cm$^2$, such as from $0.5$ cm$^2$ to $7$ cm$^2$ and including from $1$ cm$^2$ to $5$ cm$^2$. The number of photodetectors in the subject systems may vary, as desired. For example, the subject systems may include one photodetector or more, such as 2 photodetectors or more, such as 3 photodetectors or more, such as 4 photodetectors or more, such as 5 photodetectors or more, such as 10 photodetectors or more, such as 25 photodetectors or more and including 50 photodetectors or more. In certain embodiments, systems include 24 photodetectors. In other embodiments, systems include one or more photodetector arrays, where each array may include 2 or more photodetectors, such as 5 or more photodetectors, such as 10 or more photodetectors and including 25 or more photodetectors. The photodetectors in the array may be arranged in a random configuration or may be in a non-random configuration, such as having a predetermined shape, including but not limited to arranging the photodetectors into a circle, oval, square, triangle, pentagon, hexagon, or other polygon. In certain embodiments, photodetector arrays are arranged into a grid pattern.

Where the subject systems include more than one photodetector, each photodetector may be the same, or the collection of two or more photodetectors may be a combination of different photodetectors. For example, where the subject systems include two photodetectors, in some embodiments the first photodetector is a CCD-type device and the second photodetector (or imaging sensor) is a CMOS-type device. In other embodiments, both the first and second photodetectors are CCD-type devices. In yet other embodiments, both the first and second photodetectors are CMOS-type devices. In still other embodiments, the first photodetector is a CCD-type device and the second photodetector is a photomultiplier tube. In still other embodiments, the first photodetector is a CMOS-type device and the second photodetector is a photomultiplier tube. In yet other embodiments, both the first and second photodetectors are photomultiplier tubes.

In embodiments of the present disclosure, detectors of interest are configured to measure collected light at one or more wavelengths, such as at 2 or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring light emitted by a sample in the flow stream at 400 or more different wavelengths.

In some embodiments, detectors of interest are configured to measure collected light over a range of wavelengths (e.g., 200 nm-1000 nm). In certain embodiments, detectors of interest are configured to collect spectra of light over a range of wavelengths. For example, systems may include one or more detectors configured to collect spectra of light over one or more of the wavelength ranges of 200 nm-1000 nm. In yet other embodiments, detectors of interest are configured to measure light emitted by a sample in the flow stream at one or more specific wavelengths. For example, systems may include one or more detectors configured to measure light at one or more of 450 nm, 518 nm, 519 nm, 561 nm, 578 nm, 605 nm, 607 nm, 625 nm, 650 nm, 660 nm, 667 nm, 670 nm, 668 nm, 695 nm, 710 nm, 723 nm, 780 nm, 785 nm, 647 nm, 617 nm and any combinations thereof. In certain embodiments, one or more detectors may be configured to be paired with specific fluorophores, such as those used with the sample in a fluorescence assay.

In embodiments, the detector is configured to measure light continuously or in discrete intervals. In some instances, detectors of interest are configured to take measurements of the collected light continuously. In other instances, detectors of interest are configured to take measurements in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval. In certain embodiments, the subject systems are flow cytometric systems employing the above described optically aligned light collection system (e.g., flow cell nozzle optically aligned to an optical adjustment component) for detecting light emitted by a sample in a flow stream by total internal reflectance. Suitable flow cytometry systems and methods for analyzing samples include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem.* January; 49(pt 1):17-28; Linden, et. al., *Semin Throm Hemost.* 2004 October; 30(5):502-11; Alison, et al. *J Pathol,* 2010 December; 222(4):335-344; and Herbig, et al. (2007) *Crit Rev Ther Drug Carrier Syst.* 24(3): 203-255; the disclosures of which are incorporated herein by reference. In certain instances, flow cytometry systems of interest include BD Biosciences FACSCanto™ flow cytometer, BD Biosciences FACSVantage™, BD Biosciences FACSort™, BD Biosciences FACSCount™, BD Biosciences FACScan™, and BD Biosciences FACSCalibur™ systems, a BD Biosciences Influx™ cell sorter, BD Biosciences Jazz™ cell sorter and BD Biosciences Aria™ cell sorter or the like.

In certain embodiments, the subject systems are flow cytometer systems which incorporate one or more components of the flow cytometers described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300; 8,233,146; 8,753,573; 8,975,595; 9,092,034; 9,095,494 and 9,097,640; the disclosures of which are herein incorporated by reference.

Methods for Measuring Light Collected from an Irradiated Sample

Aspects of the disclosure also include methods for measuring light from a sample (e.g., in the flow stream in a flow cytometer). In practicing methods according to embodiments, a sample in a flow stream is irradiated with a light source and light from the sample is collected by one or more of the subject light collection systems and measured with a detector. In some embodiments, the sample is a biological sample. The term "biological sample" is used in its conventional sense to refer to a whole organism, plant, fungi or a subset of animal tissues, cells or component parts which may in certain instances be found in blood, mucus, lymphatic fluid, synovial fluid, cerebrospinal fluid, saliva, bronchoalveolar lavage, amniotic fluid, amniotic cord blood, urine, vaginal fluid and semen. As such, a "biological sample" refers to both the native organism or a subset of its tissues as well as to a homogenate, lysate or extract prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may be any type of organismic tissue, including both healthy and diseased tissue (e.g., cancerous, malignant, necrotic, etc.). In certain embodiments, the biological sample is a liquid sample, such as blood or derivative thereof, e.g., plasma, tears, urine, semen, etc., where in some instances the sample is a blood sample, including whole blood, such as blood obtained from venipuncture or fingerstick (where the blood may or may not be combined with any reagents prior to assay, such as preservatives, anticoagulants, etc.).

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

In practicing the subject methods, a sample (e.g., in a flow stream of a flow cytometer) is irradiated with light from a light source. In some embodiments, the light source is a broadband light source, emitting light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. For example, one suitable broadband light source emits light having wavelengths from 200 nm to 1500 nm. Another example of a suitable broadband light source includes a light source that emits light having wavelengths from 400 nm to 1000 nm. Where methods include irradiating with a broadband light source, broadband light source protocols of interest may include, but are not limited to, a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof.

In other embodiments, methods includes irradiating with a narrow band light source emitting a particular wavelength or a narrow range of wavelengths, such as for example with a light source which emits light in a narrow range of wavelengths like a range of 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Where methods include irradiating with a narrow band light source, narrow band light source protocols of interest may include, but are not limited to, a narrow wavelength LED, laser diode or a broadband light source coupled to one or more optical bandpass filters, diffraction gratings, monochromators or any combination thereof.

In certain embodiments, methods include irradiating the sample with one or more lasers. As discussed above, the type and number of lasers will vary depending on the sample as well as desired light collected and may be a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof. In others instances, the methods include irradiating the flow stream with a dye laser, such as a stilbene, coumarin or rhodamine laser. In yet other instances, methods include irradiating the flow stream with a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof. In still other instances, methods include irradiating the flow stream with a solid-state laser, such as a ruby laser, an Nd:YAG laser, NdCrYAG laser, Er:YAG laser, Nd:YLF laser, Nd:YVO$_4$ laser, Nd:YCa$_4$O(BO$_3$)$_3$ laser, Nd:YCOB laser, titanium sapphire laser, thulim YAG laser, ytterbium YAG laser, ytterbium$_2$O$_3$ laser or cerium doped lasers and combinations thereof.

The sample may be irradiated with one or more of the above mentioned light sources, such as 2 or more light sources, such as 3 or more light sources, such as 4 or more light sources, such as 5 or more light sources and including 10 or more light sources. The light source may include any combination of types of light sources. For example, in some embodiments, the methods include irradiating the sample in the flow stream with an array of lasers, such as an array having one or more gas lasers, one or more dye lasers and one or more solid-state lasers.

The sample may be irradiated with wavelengths ranging from 200 nm to 1500 nm, such as from 250 nm to 1250 nm, such as from 300 nm to 1000 nm, such as from 350 nm to 900 nm and including from 400 nm to 800 nm. For example, where the light source is a broadband light source, the sample may be irradiated with wavelengths from 200 nm to 900 nm. In other instances, where the light source includes a plurality of narrow band light sources, the sample may be irradiated with specific wavelengths in the range from 200 nm to 900 nm. For example, the light source may be plurality of narrow band LEDs (1 nm-25 nm) each independently emitting light having a range of wavelengths between 200 nm to 900 nm. In other embodiments, the narrow band light source includes one or more lasers (such as a laser array) and the sample is irradiated with specific wavelengths ranging from 200 nm to 700 nm, such as with a laser array having gas lasers, excimer lasers, dye lasers, metal vapor lasers and solid-state laser as described above.

Where more than one light source is employed, the sample may be irradiated with the light sources simultaneously or sequentially, or a combination thereof. For example, the sample may be simultaneously irradiated with each of the light sources. In other embodiments, the flow stream is sequentially irradiated with each of the light sources. Where more than one light source is employed to irradiate the sample sequentially, the time each light source irradiates the sample may independently be 0.001 microseconds or more, such as 0.01 microseconds or more, such as 0.1 microseconds or more, such as 1 microsecond or more, such as 5 microseconds or more, such as 10 microseconds or more, such as 30 microseconds or more and including 60 microseconds or more. For example, methods may include irradiating the sample with the light source (e.g. laser) for a duration which ranges from 0.001 microseconds to 100 microseconds, such as from 0.01 microseconds to 75 microseconds, such as from 0.1 microseconds to 50 microseconds, such as from 1 microsecond to 25 microseconds and including from 5 microseconds to 10 microseconds. In embodiments where sample is sequentially irradiated with two or more light sources, the duration sample is irradiated by each light source may be the same or different.

The time period between irradiation by each light source may also vary, as desired, being separated independently by a delay of 0.001 microseconds or more, such as 0.01 microseconds or more, such as 0.1 microseconds or more, such as 1 microsecond or more, such as 5 microseconds or more, such as by 10 microseconds or more, such as by 15 microseconds or more, such as by 30 microseconds or more and including by 60 microseconds or more. For example, the time period between irradiation by each light source may range from 0.001 microseconds to 60 microseconds, such as from 0.01 microseconds to 50 microseconds, such as from 0.1 microseconds to 35 microseconds, such as from 1 microsecond to 25 microseconds and including from 5 microseconds to 10 microseconds. In certain embodiments, the time period between irradiation by each light source is 10 microseconds. In embodiments where sample is sequentially irradiated by more than two (i.e., 3 or more) light sources, the delay between irradiation by each light source may be the same or different.

The sample may be irradiated continuously or in discrete intervals. In some instances, methods include irradiating the sample in the sample with the light source continuously. In other instances, the sample in is irradiated with the light source in discrete intervals, such as irradiating every 0.001 millisecond, every 0.01 millisecond, every 0.1 millisecond, every 1 millisecond, every 10 milliseconds, every 100 milliseconds and including every 1000 milliseconds, or some other interval.

Depending on the light source, the sample may be irradiated from a distance which varies such as 0.01 mm or more, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more. Also, the angle or irradiation may also vary, ranging from 10° to 90°, such as from 15° to 85°, such as from 20° to 80°, such as from 25° to 75° and including from 30° to 60°, for example at a 90° angle.

As discussed above, in embodiments light from the irradiated sample is conveyed through an optically aligned light collection system as described herein and measured by one or more detectors. In practicing the subject methods, light is propagated through the mount and connectors. The light is then passed through one or more pinholes in an orifice plate at the distal end of the connector and into an optical collection system. Light from the optical collection system is directed to a detector which measures the collected light at one or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring the collected light at 400 or more different wavelengths.

In some embodiments, methods include measuring the collected light over a range of wavelengths (e.g., 200 nm-1000 nm). For example, methods may include collecting spectra of light over one or more of the wavelength ranges of 200 nm-1000 nm. In yet other embodiments, methods include measuring collected light at one or more specific wavelengths. For example, the collected light may be measured at one or more of 450 nm, 518 nm, 519 nm, 561 nm, 578 nm, 605 nm, 607 nm, 625 nm, 650 nm, 660 nm, 667 nm, 670 nm, 668 nm, 695 nm, 710 nm, 723 nm, 780 nm, 785 nm, 647 nm, 617 nm and any combinations thereof. In certain embodiments, methods including measuring wavelengths of light which correspond to the fluorescence peak wavelength of certain fluorophores.

The collected light may be measured continuously or in discrete intervals. In some instances, methods include taking measurements of the light continuously. In other instances, the light is measured in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval.

Measurements of the collected light may be taken one or more times during the subject methods, such as 2 or more times, such as 3 or more times, such as 5 or more times and including 10 or more times. In certain embodiments, the light propagation is measured 2 or more times, with the data in certain instances being averaged.

Light measurements may be taken with any convenient protocol, including but not limited to optical sensors or photodetectors, such as active-pixel sensors (APSs), avalanche photodiode, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, the transmitted light is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors. In certain embodiments, light is measured with a charge-coupled device (CCD). Where the transmitted light is measured with a CCD, the active detecting surface area of the CCD may vary, such as from 0.01 $cm^2$ to 10 $cm^2$, such as from 0.05 $cm^2$ to 9 $cm^2$, such as from, such as from 0.1 $cm^2$ to 8 $cm^2$, such as from 0.5 $cm^2$ to 7 $cm^2$ and including from 1 $cm^2$ to 5 $cm^2$.

In some embodiments, methods include adjusting the light before measurement with the detector. For example, the collected light may be passed through one or more additional lenses, mirrors, pinholes, slits, gratings, light refractors, and any combinations thereof. In some instances, the collected light is passed through one or more focusing lenses, such as to reduce the profile of the light directed onto the active surface of the detector. In other instances, the emitted light from the sample is passed through one or more de-magnifying lenses, such as to increase the profile of the light directed onto the active surface of the detector.

In yet other instances, methods include further collimating the light. For example, light propagated through the subject optically aligned light collection systems may be further collimated by passing the light through one or more collimating lenses or with collimating mirrors or a combination thereof. In still other instances, methods further include passing light propagated through the subject optically aligned light collection systems through one or more wavelength separators. Wavelength separation, according to certain embodiments, may include selectively passing or blocking specific wavelengths or wavelength ranges of the polychromatic light. To separate wavelengths of light, the light may be passed through any convenient wavelength separating protocol, including but not limited to colored glass, bandpass filters, interference filters, dichroic mirrors, diffraction gratings, monochromators and combinations thereof, among other wavelength separating protocols.

Kits

Aspects of the invention further include kits, where kits include one or more connectors, adapters for coupling the connector to the mount, adapters for coupling an orifice plate to the connector, adapters for coupling an optical collection component to the connector, optical adjustment components, orifice plates and optical collection components (e.g., fiber optics light relay systems or free-space light relay system) as described herein.

In some embodiments, kits include 2 or more of the components of the light collection systems disclosed herein, such as 3 or more and including 5 or more. In some embodiments, kits include a first connector that has a distal end that is configured for coupling to a fiber optics light relay system and a second connector that has a distal end that is configured for coupling to a free-space light relay system.

In some instances, the kits can include one or more assay components (e.g., labeled reagents, buffers, etc., such as described above). In some instances, the kits may further include a sample collection device, e.g., a lance or needle configured to prick skin to obtain a whole blood sample, a pipette, etc., as desired.

The various assay components of the kits may be present in separate containers, or some or all of them may be pre-combined. For example, in some instances, one or more components of the kit, e.g., the connectors, orifice plates are present in a sealed pouch, e.g., a sterile foil pouch or envelope.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

Utility

The subject optically aligned light collection systems and methods for assembling and using thereof find use in a variety of application where is it is necessary or desirable to interchange between different types of optical collection systems, such as between a fiber optics light relay system and a free-space light relay system without subsequent re-alignment or calibration. In addition, the subject systems and methods find use in increasing the amount of light collected from a sample in a flow stream. In certain instances, the present disclosure finds use in enhancing measurement of light collected from a sample that is irradiated in a flow stream in a flow cytometer. Embodiments of the present disclosure find use where enhancing the effectiveness of emission measurements in flow cytometry are desired, such as in research and high throughput laboratory testing. The present disclosure also finds use where it is desirable to provide a flow cytometer with improved cell sorting accuracy, enhanced particle collection, reduced energy consumption, particle charging efficiency, more accurate particle charging and enhanced particle deflection during cell sorting.

The present disclosure also finds use in applications where cells prepared from a biological sample may be desired for research, laboratory testing or for use in therapy. In some embodiments, the subject methods and devices may facilitate the obtaining individual cells prepared from a target fluidic or tissue biological sample. For example, the subject methods and systems facilitate obtaining cells from fluidic or tissue samples to be used as a research or diagnostic specimen for diseases such as cancer. Likewise, the subject methods and systems facilitate obtaining cells from fluidic or tissue samples to be used in therapy. Methods and devices of the present disclosure allow for separating and collecting cells from a biological sample (e.g., organ, tissue, tissue fragment, fluid) with enhanced efficiency and low cost as compared to traditional flow cytometry systems.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A light collection system comprising:
    a mount comprising a proximal end and a distal end:
        an orifice for receiving light at the proximal end of the mount;
        an adapter configured for coupling to a camera; and
        a first fastener for attaching a lens to a distal end of the mount; and
    a connector comprising a proximal end and a distal end, wherein the proximal end of the connector is configured to be coupled to the distal end of the mount and the distal end of the connector is configured to be coupled to an orifice plate, the connector comprising:
        an aligner; and
        a second fastener that releasably couples the proximal end of the connector to the distal end of the mount and maintains optical alignment between the mount, the orifice plate and an optical collection component.

2. The light collection system according to claim 1, further comprising an orifice plate positioned between the connecter and the optical collection component.

3. The light collection system according to claim 2, wherein the orifice plate is configured to be releasably attached to one or more of the connector and the optical collection component.

4. The light collection system according to claim 3, wherein the orifice plate is configured to be releasably attached to the connector and the optical collection component.

5. The light collection system according to claim 2, wherein the orifice plate comprises a pinhole mirror.

6. The light collection system according to claim 2, wherein the orifice plate comprises 5 or more orifices.

7. The light collection system according to claim 2, wherein the orifice plate comprises a slit.

8. The light collection system according to claim 7, wherein the free-space light relay system comprises a prism.

9. The light collection system according to claim 1, further comprising an optical collection component.

10. The light collection system according to claim 9, wherein the optical collection component is a fiber optics light relay bundle.

11. The light collection system according to claim 9, wherein the optical collection component is a free-space light relay system.

12. The light collection system according to claim 11, wherein the free-space light relay system comprises a wavelength separator.

13. The light collection system according to claim 1, wherein the aligner is an alignment component selected from the group consisting of a protrusion, a dowel, a groove, a notch, a countersink, a counter-bore and a hole.

14. The light collection system according to claim 13, wherein the aligner is a dowel.

15. The light collection system according to claim 14, wherein the aligner is a press-fit dowel.

16. The light collection system according to claim 1, wherein the first and second fasteners are independently selected from the group consisting of a magnet, a latch, a hinge, a tether, a hook and loop fastener and a screw thread.

17. The light collection system according to claim 16, wherein the first and second fasteners are screw threads.

18. The light collection system according to claim 1, wherein the distal end of the mount comprises an aligner that is configured to couple with an aligner at the distal end of the connector.

19. The light collection system according to claim 18, further comprising a fastener that releasably couples the aligner at the distal end of the mount to the aligner at the distal end of the connector.

20. The light collection system according to claim 1, wherein the mount and connector are concentric and aligned along the same longitudinal axis.

21. A system comprising:
  a light source;
  a light collection system comprising:
    a mount comprising a proximal end and a distal end:
      an orifice for receiving light at the proximal end of the mount;
      an adapter configured for coupling to a camera; and
      a first fastener for attaching a lens to a distal end of the mount; and
    a connector comprising a proximal end and a distal end, wherein the proximal end of the connector is configured to be coupled to the distal end of the mount and the distal end of the connector is configured to be coupled to an orifice plate, the
      connector comprising:
        an aligner; and
        a second fastener that releasably couples the proximal end of the connector to the distal end of the mount and maintains optical alignment between the mount, the orifice plate and an optical collection component; and
  a detector for measuring one or more wavelengths of light from the optical collection component.

22. A method comprising:
  irradiating a sample in a flow stream in an interrogation field with a light source;
  collecting light emitted by the sample in the flow stream through a light collection system comprising:
    a mount comprising a proximal end and a distal end:
      an orifice for receiving light at the proximal end of the mount;
      an adapter configured for coupling to a camera; and
      a first fastener for attaching a lens to a distal end of the mount; and
    a connector comprising a proximal end and a distal end, wherein the proximal end of the connector is configured to be coupled to the distal end of the mount and the distal end of the connector is configured to be coupled to an orifice plate, the connector comprising:
      an aligner; and
      a second fastener that releasably couples the proximal end of the connector to the distal end of the mount and maintains optical alignment between the mount and an optical collection component; and
  measuring the collected light at one or more wavelengths.

23. A kit comprising:
  a mount comprising a proximal end and a distal end:
    an orifice for receiving light at the proximal end of the mount;
    an adapter configured for coupling to a camera; and
    a first fastener for attaching a lens to a distal end of the mount;
  a connector comprising a proximal end and a distal end, wherein the proximal end of the connector is configured to be coupled to the distal end of the mount and the distal end of the connector, the connector comprising:
    an aligner; and
    a second fastener that releasably couples the proximal end of the connector to the distal end of the mount and maintains optical alignment between the mount and an optical collection component; and
  two or more orifice plates.

* * * * *